(12) United States Patent
Dykstra et al.

(10) Patent No.: US 7,410,989 B2
(45) Date of Patent: Aug. 12, 2008

(54) COMPOUNDS, METHODS AND COMPOSITIONS USEFUL FOR THE TREATMENT OF BOVINE VIRAL DIARRHEA VIRUS (BVDV) INFECTION AND HEPATITIS C VIRUS (HCV) INFECTION

(75) Inventors: Christine C. Dykstra, Auburn, AL (US); Maurice Daniel Givens, Auburn, AL (US); David A. Stringfellow, Auburn, AL (US); Kenny Brock, Auburn, AL (US); David Boykin, Atlanta, GA (US); Arvid Kumar, Atlanta, GA (US); W. David Wilson, Atlanta, GA (US); Richard R. Tidwell, Pittsboro, NC (US); Chad F. Stephens, Villa Roca, GA (US)

(73) Assignees: The University of North Carolina at Chapel Hill, Chapel Hill, NC (US); Georgia State University Research Foundation, Inc., Atlanta, GA (US); Auburn University, Auburn, AL (US)

( * ) Notice: Subject to any disclaimer, the term of this patent is extended or adjusted under 35 U.S.C. 154(b) by 0 days.

(21) Appl. No.: 11/602,031

(22) Filed: Nov. 20, 2006

(65) Prior Publication Data

US 2007/0072878 A1    Mar. 29, 2007

Related U.S. Application Data

(60) Division of application No. 11/262,427, filed on Oct. 28, 2005, now Pat. No. 7,163,955, which is a division of application No. 10/796,657, filed on Mar. 9, 2004, now Pat. No. 7,183,286, which is a continuation of application No. 10/044,315, filed on Jan. 11, 2002, now abandoned.

(60) Provisional application No. 60/261,654, filed on Jan. 13, 2001.

(51) Int. Cl.
*A61K 31/4184* (2006.01)
*C07D 235/06* (2006.01)
*C07D 403/14* (2006.01)
*C07C 257/10* (2006.01)
*C07C 257/18* (2006.01)

(52) U.S. Cl. .................. 514/394; 548/306.1; 548/304.7; 564/244

(58) Field of Classification Search ................ 514/394; 548/306.1, 304.7; 564/244
See application file for complete search history.

(56) References Cited

U.S. PATENT DOCUMENTS

| 2,641,601 | A |  | 6/1953 | Goldberg et al. |
| 4,153,703 | A |  | 5/1979 | Harrison et al. |
| 5,602,172 | A |  | 2/1997 | Boykin et al. |
| 5,667,975 | A |  | 9/1997 | Dykstra et al. |
| 5,668,165 | A |  | 9/1997 | Wuonola et al. |
| 5,723,288 | A |  | 3/1998 | Dykstra et al. |
| 5,935,776 | A |  | 8/1999 | Green et al. |
| 5,958,950 | A | * | 9/1999 | Padia et al. .................. 514/321 |
| 6,008,247 | A |  | 12/1999 | Boykin et al. |
| 6,613,787 | B2 |  | 9/2003 | Wilson et al. |
| 6,635,668 | B1 |  | 10/2003 | Tidwell et al. |
| 6,774,144 | B1 |  | 8/2004 | Dykstra et al. |
| 6,867,227 | B2 | * | 3/2005 | Wilson et al. ............... 514/375 |
| 7,160,914 | B2 | * | 1/2007 | Wilson et al. ............... 514/393 |
| 2002/0156098 | A1 |  | 10/2002 | Werbovetz et al. |
| 2003/0083362 | A1 |  | 5/2003 | Boykin et al. |
| 2004/0053481 | A1 |  | 3/2004 | Wilson et al. |
| 2005/0158785 | A1 |  | 7/2005 | Wilson et al. |

FOREIGN PATENT DOCUMENTS

| BE | 641607 |  | 6/1964 |
| EP | 941991 | A1 | 9/1999 |
| FR | 1464999 |  | 12/1965 |
| GB | 1084175 |  | 9/1967 |
| JP | 54014970 |  | 2/1979 |
| JP | 179856 |  | 7/1995 |
| WO | WO 9615126 | A1 | 5/1996 |
| WO | WO 01/03685 | A2 | 1/2001 |
| WO | WO 0132159 | A2 | 5/2001 |
| WO | WO 01/46175 | A | 6/2001 |
| WO | 02/36588 |  | 5/2002 |

OTHER PUBLICATIONS

Communication pursuant to Rule 44a EPC corresponding to European application No. 07110507.6-2117 dated Oct. 17, 2007.

(Continued)

*Primary Examiner*—Rebecca L Anderson
*Assistant Examiner*—Jason M Nolan
(74) *Attorney, Agent, or Firm*—Jenkins, Wilson, Taylor & Hunt, P.A.

(57) ABSTRACT

The present invention relates to novel compounds and methods that are useful in treating members of the Flaviviridae family of viruses. Compounds of the present invention will have a structure according to Formulas (I)-(VI) as recited throughout the application.

38 Claims, 1 Drawing Sheet

OTHER PUBLICATIONS

European Office Action corresponding to EP application No. 02 705 743.9-2117 dated May 26, 2006.
Australian First Report corresponding to Australian Patent Application No. 2002239873 dated Oct. 21, 2005.
European Search Report for corresponding European app. No. 02705743.9 dated Jul. 15, 2005.
Givens et al. *Anti Microbial Agents and Chemotherapy*, 47(7): 2223-2230, 2003.
International Search Report for PCT/US02/00787 (Sep. 12, 2002).
Lansiaux et al., *Journal of Medicinal Chemistry*, 45: 1994-2002, 2002.
Davis et al., CA 134:39002, 2000.
Wang et al., "Evaluation of the Infulence of Compound Structure on Stacked-Dimer Formation in the DNA Minor Groove", *Biochemistry*, 40: 2511-2521, 2001.
Wang et al., "Specific Molecular Recognition of Mixed Nucleic Acid Sequences: An Aromatic Dication that Binds in the DNA minor Groove as a Dimer", *PNAS*, 97 (1): 12-16, Jan. 4, 2000.
Gelus et al., "Inhibition of HIV-1 Tat-TAR Interaction by Diphenylfuran Derivatives: Effects of the Terminal Basic Side Chains", *Bioorganic & Medicinal Chemistry*, 7: 1089-1096, 1999.
Del Poeta et al. "In Vitro Antifungal Activities of a Series of Dication-Substituted Carbazoles, Furans, and Benzimidazoles", *Antimicrobial Agents and Chemotherapy*, 42(10): 2503-2510, Oct. 1998.
Blagburn et al., CA 129:297986, 1998.
Boykin et al., "2,5-Bis[4-(N-alkylamidino)phenyl]furans as Anti-Pneumocystis carinii Agents," Journal of Medicinal Chemistry (1998), 41 (1), pp. 124-129.
Zapp et al., "Modulation of the Rev-RRE Interaction by Aromatic Heterocyclic Compounds", *Bioorganic & Medicinal Chemistry*, 5 (6): 1149-1155, 1997.
Neidle et al., CA 127:103988, 1997.
Boykin et al., "Anti-Pneumocystis Activity of Bis-Amidoximes and Bis-O-Alkylamidoximes Prodrugs", *Bioorganic & Medicinal Chemistry Letters*, 6 (24): 3017-3020, 1996.
Ratmeyer et al., "Inhibition of HIV-1 Rev-RRE Interaction by Diphenylfuran Derivatives", *Biochemistry*, 35: 13689-13696, 1996.
Boykin et al., "Dicationic Diarylfurans as Anti-Pneumocystis carinii Agents," CA 122:230122, 1995.
Tralic-Kulenovic et al., "Synthesis and Absorption Spectral Properties of Substituted Phenylfurylbenzothiazoles and their Vinylogues", *Monatshefte fur Chemie*, 125: 209-215, 1994.
Steck et al., "Leishmania donovani, Plasmodium berghei, Trypanosoma rhodesiense: antiprotozoal effects of some admidine types," CA 96:135352, 1982.
De Clereq et al., "Diaryl Amidine Derivatives as Oncornaviral DNA Polymerase Inhibitors", *J. Med. Chem.*, 23: 787-795, 1980.
Das et al., "Synthesis and Antiprotozoal Activity of 2,5-Bis(4-guanylphenyl)furans," Journal of Medicinal Chemistry (1977), 20(4), pp. 531-536.
Official Action corresponding to an Japanese Patent Application No. 2002555762 dated Jan. 22, 2008.

* cited by examiner

SCHEME 1

Legend for compounds 2-5:
a: $X_1 = H, X_2 = H$
b: $X_1 = Me, X_2 = H$
c: $X_1 = OMe, X_2 = H$
d: $X_1 = Cl, X_2 = H$
e: $X_1 = CF_3, X_2 = H$
f: $X_1 = Me, X_2 = Me$ (a) Pd(PPh$_3$)$_4$, 1,4-dioxane, Δ
(b) H$_2$, Pd/C, EtOAc, EtOH
(c) SnCl$_2$ dihydrate, EtOH, DMSO Δ

SCHEME 2

SEQUENCE LISTING

<160> NUMBER OF SEQ ID NOS: 3

<210> SEQ ID NO 1
<211> LENGTH: 18
<212> TYPE: DNA
<213> ORGANISM: Bovine Viral Diarrhea Virus

<400> SEQUENCE: 1
ggctagccat gcccttag                                               18

<210> SEQ ID NO 2
<211> LENGTH: 17
<212> TYPE: DNA
<213> ORGANISM: Hepatitis C virus

<400> SEQUENCE: 2
ccatgtgcca tgtacag                                                17

<210> SEQ ID NO 3
<211> LENGTH: 22
<212> TYPE: DNA
<213> ORGANISM: Artificial Sequence
<220> FEATURE:
<223> OTHER INFORMATION: Synthetic degenerate primer based on Bovine
      Viral Diarrhea Virus to accommodate differences within the 5'
      untranslated sequences of virus strains
<220> FEATURE:
<221> NAME/KEY: misc_feature
<222> LOCATION: (14)..(14)
<223> OTHER INFORMATION: Nucleotide 14 is degenerate (d is a, g, or t)
      to accomodate differences within the 5' untranslated sequences of
      virus strains used in this research

<400> SEQUENCE: 3
cctgagtaca gggdagtcgt ca                                          22

COMPOUNDS, METHODS AND COMPOSITIONS USEFUL FOR THE TREATMENT OF BOVINE VIRAL DIARRHEA VIRUS (BVDV) INFECTION AND HEPATITIS C VIRUS (HCV) INFECTION

CROSS REFERENCE TO RELATED APPLICATIONS

The present application is a divisional of U.S. patent application Ser. No. 11/262,427, filed on Oct. 28, 2005, now U.S. Pat. No. 7,163,955 herein incorporated by reference in its entirety, which is a divisional of U.S. patent application Ser. No. 10/796,657, filed on Mar. 9, 2004, now U.S. Pat. No. 7,183,286 herein incorporated by reference in its entirety, which is a continuation of U.S. patent application Ser. No. 10/044,315, filed Jan. 11, 2002, now abandoned, the disclosure of which is incorporated herein by reference in its entirety, which claims priority to U.S. Provisional Application No. 60/261,654, filed Jan. 13, 2001, the disclosure of which is incorporated herein by reference in its entirety.

STATEMENT OF GOVERNMENT SUPPORT

This invention was made with government support under grant number K08 AI01728-01 and U0I-A133383 from the National Institutes of Health. The United States government may have certain rights in this invention.

FIELD OF THE INVENTION

This invention relates to the treatment of bovine viral diarrhea virus (BVDV) and hepatitis C virus (HCV) infections.

BACKGROUND OF THE INVENTION

Bovine viral diarrhea virus (BVDV) is an enveloped, single-stranded, positive sense RNA virus in the genus Pestivirus and the family Flaviviridae. Based on the presence or absence of visible cytopathic effect when susceptible cell monolayers are infected, two pathogenic biotypes of BVDV, referred to as cytopathic and noncytopathic, have been identified. Perdrizet J A in: B. P. Smith (ed), *Large Animal Internal Medicine, First Edition* (Mosby Press, St Louis, 731-737 (1990)). A differentiation is also made between biotypes of BVDV (referred to as biotypes I and II) based on certain viral RNA sequences in the 5' untranslated region of the genome. Pellerin C, et al., *Virology* 203, 260-268 (1994); J. F. Ridpath et al., *Virology* 205, 66-74 (1994).

BVDV may cause acute infection in cattle, resulting in bovine respiratory disease, diarrhea and severe reproductive losses. Clinical symptoms of acute BVDV infection may range from the almost undetectable to the severe. Infection of pregnant cows and heifers may result in breeding problems (e.g., irregular heats), abortion, premature births or the birth of weak or stunted calves. In some cases, temporary damage to an animal's immune system may occur even when the clinical symptoms are not apparent. In addition to the illness caused by the virus itself, infected animals are more susceptible and are more likely to suffer from other diseases, such as pneumonia.

In addition to causing acute disease, BVDV may also establish persistent infections. Potgieter, *Vet. Clin. North Am. Food Anim. Pract* 11, 501-520 (1995). Persistent BVDV infections are generally established via in utero infection of a developing fetus with a noncytopathic BVDV. The resulting animals are born immunotolerant of the particular BVDV by which they are infected, and may continually shed virus throughout their life span. While some persistently infected animals exhibit congenital malformations due to BVDV infection, many animals persistently infected with BVDV appear clinically normal. Baker, *Rev. Sci. Tech* 9, 25-41 (1990); Bielefeldt-Ohmann, *Vet. Clin. North Am. Food Anim. Pract* 11, 447-476 (1995). Persistently infected animals are thought to be the major disseminators of BVDV in the cattle population.

There are more than 140 vaccines against BVDV commercially available in the United States. Bolin, *Am J. Vet Res.* 46, 2476-2470 (1995). Unfortunately, vaccination does not provide complete protection against BVDV infection, as some vaccinated cattle still become infected with the virus. At present, there is no known cure for BVDV infection. Accordingly, a need exists for an effective treatment for BVDV infection.

In vitro production of embryos has become a useful therapy for increasing reproductive performance of animals and for treating infertility of both animals and humans. In vitro production of bovine embryos could permit the humane, worldwide transfer of genetic material among cattle while limiting the transmission of many pathogens. However, in vitro-produced bovine embryos are potential vectors for transmission of BVDV. B. Avery et al., *Vet Rec* 132, 660 (1993); A. Bielanski et al., *Theriogenology* 46, 1467-1476 (1996); T. Tsuboi et al., *Vet Microbiol* 49, 127-134 (1996); O. Zurovac et al., *Theriogenology* 41, 841-853 (1994). BVDV can be introduced into the embryo production system in association with gametes, serum, somatic cells, cumulus oocyte complexes (COCs), and result in contaminated in vitro fertilized (IVF) embryos or cell lines. K. V. Brock et al., *J Vet Diagn Invest* 3, 99-100 (1991); C. R. Rossi et al., *Am J Vet Res* 41, 1680-1681 (1980); P. J. Booth et al., *J Reprod Fert* Abstr Ser Suppl 9, 28 (1992); M. D. Fray et al., *Vet Pathol* 35, 253-259 (1998); R. Harasawa et al., *Microbiol Immunol* 39, 979-985 (1995); T. Shin et al., *Theriogenology* 53, 243 (2000). Association of noncytopathic BVDV with transferred IVF embryos may cause infection of embryo recipients, early embryonic death, abortion or birth of persistently infected offspring.

An analogous hazard exists in human in vitro embryo production. Viral transmission to human embryos and embryo recipients by means of contaminated embryo culture media has been reported. Addition of an anti-viral agent to the culture medium surrounding in vitro-produced embryos could prevent or reduce transmission of virus to the embryo or embryo recipient. P. M. Grosheide et al., *Vaccine* 9, 682-687 (1991); W. G. Quint et al., *J Clin Microbiol* 32, 1099-1100 (1994); H. C. van Os et al., *Am J Obstet Gynecol* 165, 152-159 (1991). Accordingly, an antiviral agent that could be added to both animal and human in vitro embryo production systems may have important applications.

The organization of the portion of the BVDV genome that encodes the proteins used in viral replication is very similar to that of human hepatitis C virus (HCV), another flavivirus. S. W. Behrens et al., *J Virol* 72, 2364-2372 (1998). It is believed that more than 80% of the individuals infected with HCV will eventually develop a chronic form of the disease. As the disease develops, the liver of the infected subject is progressively damaged, with the symptoms generally being commensurate with cirrhosis and liver failure (e.g., jaundice, abdominal swelling, and finally, coma). The cycle of disease from infection to significant liver damage can take 20 years or more. Liver failure due to HCV is the presently the leading cause of liver transplants in the United States. It is suspected that there are, at present, more than 5 million people in the United States that are infected with HCV, and perhaps as many as 200 million around the world, making HCV infection a significant public health threat.

The development of a vaccine for HCV infection is uncertain, due in part to the high mutation rate of the virus. Recombinant interferon alpha-2b (INTRON A®/Schering) has proved effective in some cases of chronic hepatitis C. However, it has been reported that relapse occurs in at least half the responders after the interferon alpha-2b treatment is discontinued. Additionally, interferon alpha-2b may exacerbate hepatocyte injury caused by autoimmune chronic active hepatitis. J. Y. N. Lau et al., *Br Med J.* 306, 469-470 (1993). The nucleotide analog ribavirin (VIRAZOLE®/ICN Pharmaceuticals) has been shown to reduce concentrations of hepatitis C viral RNA in an infected subject, although at a slower rate than interferon alpha-2b. As with BVDV infection, a need exists for an effective treatment for HCV infection.

SUMMARY OF THE INVENTION

In view of the foregoing, one aspect of the invention relates to novel compounds that are useful in treating members of the Flaviviridae family of viruses, such as bovine viral diarrhea virus (BVDV) infection and hepatitis C virus (HCV) infection. Compounds of the present invention will have a structure according to Formulas (I)-(VI), as follows:

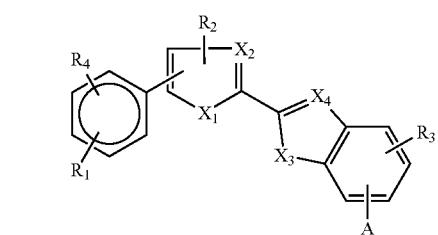
(I)

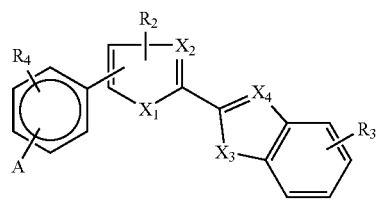
(II)

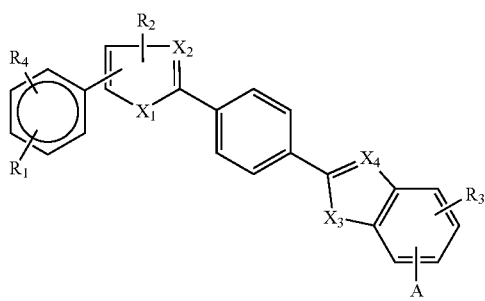
(III)

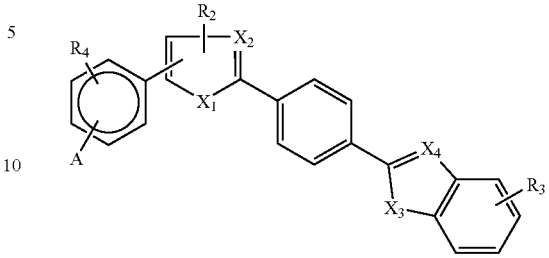
(IV)

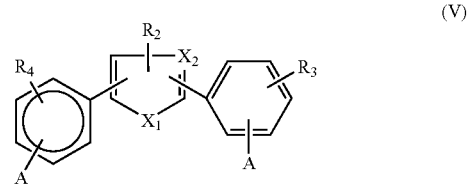
(V)

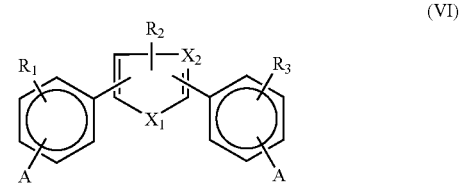
(VI)

wherein:

$X_1$ and $X_3$ are each independently selected from the group consisting of O, S and $NR_9$, wherein $R_9$ is H or alkyl;

$X_2$ and $X_4$ are each independently CH or N;

A is selected from the group consisting of H, alkyl, aryl,

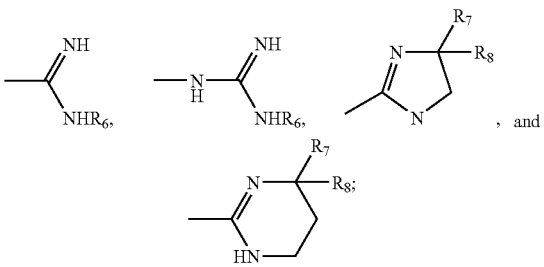

$R_1, R_2, R_3, R_4$ and $R_5$ are each independently selected from the group consisting of H, alkyl, alkoxy, amidine, halide, alkylhalide, nitro and amino groups;

$R_6$ is H, alkyl or aryl; and $R_7$ and $R_8$ are each independently selected from the group consisting of H and alkyl.

Additional aspects of the invention include pharmaceutical compositions comprising a compound having a structure according to Formulas (I)-(VI), or a pharmaceutical salt thereof (i.e., an "active compound"), in a pharmaceutically acceptable carrier. Pharmaceutical compositions of the present invention are useful in the treatment of bovine viral disease virus (BVDV) infection and hepatitis C virus (HCV) infection.

Certain aspects of the invention relate to methods of treating bovine viral disease virus (BVDV) infection in a subject in need of such treatment. The method comprises administering to the subject a compound according to Formulas (I) through (VI), or a pharmaceutically acceptable salt thereof, in an amount effective to treat bovine viral disease virus (BVDV) infection.

Other aspects of the invention relate to methods of treating hepatitis C virus (HCV) infection in a subject in need of such treatment. The method comprises administering to the subject a compound according to Formulas (I) through (VI), or a pharmaceutically acceptable salt thereof, in an amount effective to treat hepatitis C virus (HCV) infection.

A further aspect of the present invention is the use of the active compounds described herein for the manufacture of a medicament for the treatment of bovine viral disease virus (BVDV) infection in a subject in need of such treatment.

Still another aspect of the present invention is the use of the active compounds described herein for the manufacture of a medicament for the treatment of treating hepatitis C virus (HCV) infection in a subject in need of such treatment.

The foregoing and other aspects of the present invention are explained in detail in the specification set forth below.

DETAILED DESCRIPTION OF THE INVENTION

Figure 1:
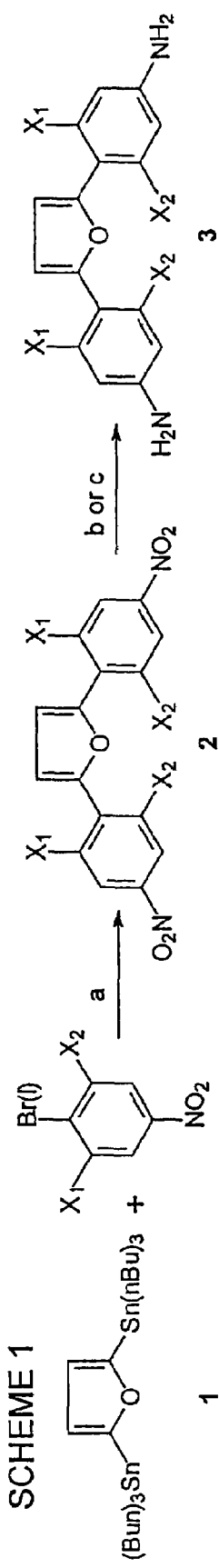
FIG. 1 illustrates four chemical schemes useful in the synthesis of compounds of the present invention.
Figure 1:
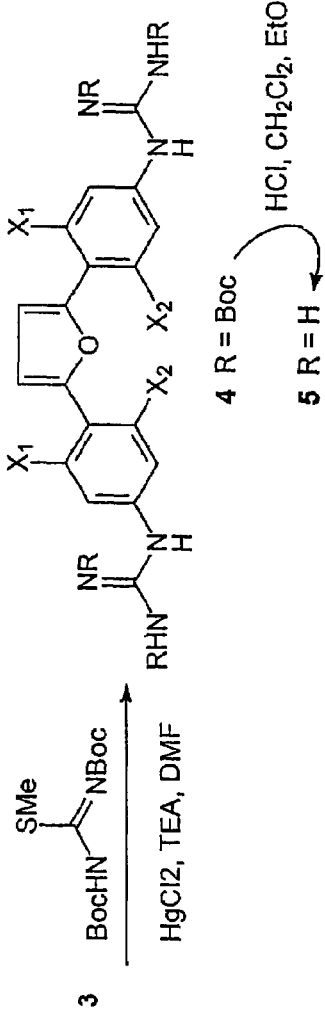

The present invention now will be described more fully hereinafter with reference to the accompanying specification and drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

With respect to the compounds of the Formulas (I) through (VI), as used herein, the term "alkyl" refers to C1-10 inclusive, linear, branched, or cyclic, saturated or unsaturated (i.e., alkenyl and alkyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. The term "alkyl" specifically includes cycloakyl hydrocarbon chains, which as used herein refers to C3 to C6 cyclic alkyl, such as cyclopropyl, cyclobutyl, cyclopentyl, and cyclohexyl. In the present invention, preferred alkyls are the lower alkyls. The term "lower alkyl" refers to C1 to C4 linear or branched alkyl, such as methyl, ethyl, propyl, butyl, isopropyl, sec-butyl, and tert-butyl.

The term "alkyl" also encompasses substituted alkyls, which include aminoalkyls, hydroalkyls, oxygen-substituted alkyls (i.e., alkoxy groups), and halogen-substituted alkyls (i.e., alkyl halides, polyhaloalkyls). The term "aminoalkyl," as used herein, refers to C1 to C4 linear or branched amino-substituted alkyl, wherein the term "amino" refers to the group NR'R", and wherein R' and R" are independently selected from H or lower alkyl as defined above, i.e., —$NH_2$, —$NHCH_3$, —$N(CH_3)2$, etc. The term "hydroxyalkyl" as used herein refers to C1 to C4 linear or branched hydroxy-substituted alkyl, i.e., —$CH_2OH$, —$(CH_2)_2OH$, etc. The term "alkoxy" as used herein refers to C1 to C4 oxygen-substituted alkyl, i.e., —$OCH_3$. The term "loweralkoxy," as used herein, refers to C1 to C4 linear or branched alkoxy, such as methoxy, ethoxy, propyloxy, butyloxy, isopropyloxy, and t-butyloxy.

The terms "halo" and "halide" have their conventional meaning and refer to fluoro, chloro, bromo, and iodo groups. Preferred halo groups include chloro groups, and preferred alkyl halides of the present invention include $CF_3$. "Nitro" groups; as used herein, have the structure —$NO_2$.

The term "aryl" as used herein refers to C3 to C10 cyclic aromatic groups such as phenyl, naphthyl, and the like, and specifically includes substituted aryl groups including but not limited to tolyl, substituted phenyl, and substituted naphthyl. Aryl groups may be substituted with halo, amino, nitro, and the like. Heterocyclic aromatic rings and polycyclic aromatic groups are also included in this definition of "aryl." Specific examples of aryl groups encompassed by the present invention include but are not limited to cyclopentadienyl, phenyl, furan, thiophene, pyrrole, pyran, pyridine, imidazole, isothiazole, isoxazole, pyrazole, pyrazine, pyrimidine, and the like.

The compounds of the present invention are also useful in the form of their pharmaceutically acceptable salt forms. Such salts may include, but are not limited to, the gluconate, lactate, acetate, tartarate, citrate, phosphate, borate, nitrate, sulfate, hydrobromide and hydrochloric salts of the compounds. Compounds of Formulas (I)-(VI) and their pharmaceutically acceptable salts are referred to herein as "active compounds" or "active agents."

The compounds represented by the Formulas (I) through (VI) may be formed by synthesis procedures that are described in the Examples below, as well as by certain methods known in the art. Some of these known methods are set forth below in the Examples by description or by reference (the disclosures of which are all incorporated herein by reference in their entirety).

Examples of compounds useful in the present invention are set forth in Table 1, below. In Table 1, the A groups are as follows:

TABLE 1

Selected Compounds Of The Present Invention

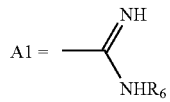

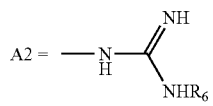

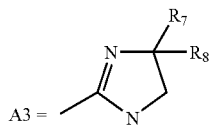

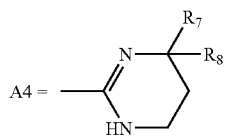

| Compound Name | Formula | A | X1 | X2 | X3 | X4 | R1 | R2 | R3 | R4 | R6 | R7 | R8 |
|---|---|---|---|---|---|---|---|---|---|---|---|---|---|
| DB 456 | I | A3 | O | C | NH | N | NH2 | H | H | H | — | H | H |
| DB 457 | I | A3 | O | C | NH | N | NO2 | H | H | H | — | H | H |
| DB 458 | I | A1 | O | C | NH | N | NO2 | H | H | H | alkyl | — | — |
| DB 459 | I | A1 | O | C | NH | N | NH2 | H | H | H | alkyl | — | — |
| DB 606 | V | A3 | O | C | — | — | OCH3 | H | H | H | H | H | H |
| DB 619 | VI | A1 | NH | C | — | — | H | H | H | — | H | — | — |
| DB 673 | VI | A2 | O | C | — | — | H | H | H | — | H | — | — |
| DB 680 | VI | A2 | O | C | — | — | CH$_3$ | H | CH$_3$ | — | H | — | — |
| DB 686 | VI | A2 | S | C | — | — | H | H | H | — | H | — | — |
| DB 687 | VI | A2 | S | N | — | — | H | H | H | — | H | — | — |
| DB 700 | VI | A2 | O | C | — | — | H | H | H | — | H | — | — |
| DB 701 | VI | A2 | O | C | — | — | CF3 | H | CF3 | — | H | — | — |
| DB 705 | VI | A2 | O | C | — | — | H | H | H | — | H | — | — |
| DB 708 | VI | A2 | O | C | — | — | Cl | H | Cl | — | H | — | — |
| DB 711 | VI | A2 | O | C | — | — | OCH$_3$ | H | OCH$_3$ | — | H | — | — |
| DB 752 | VI | A2 | S | C | — | — | CH$_3$ | H | CH$_3$ | — | H | — | — |
| DB 771 | II | A2 | O | C | NH | N | H | H | H | — | H | — | — |
| DB 772 | II | A3 | O | C | NH | N | H | H | H | — | — | H | H |

Formulas of the compounds set forth above are as follows:
DB 456
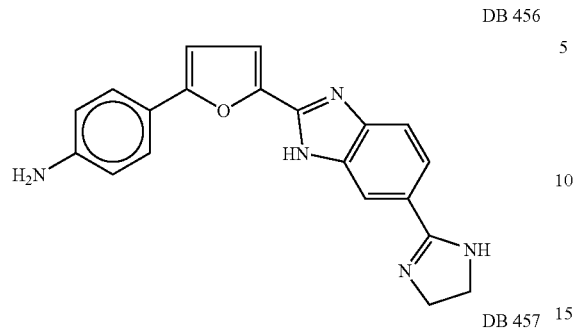
DB 619
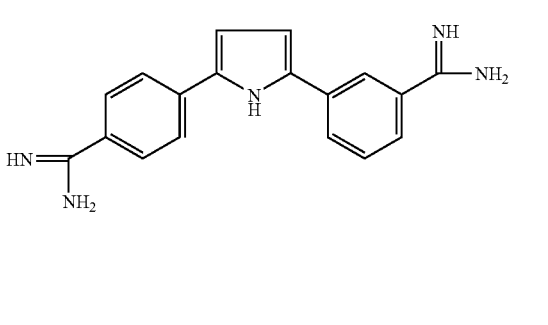
DB 457
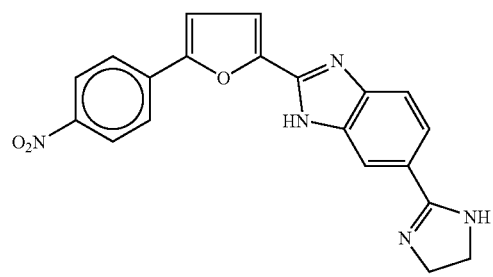
DB 673
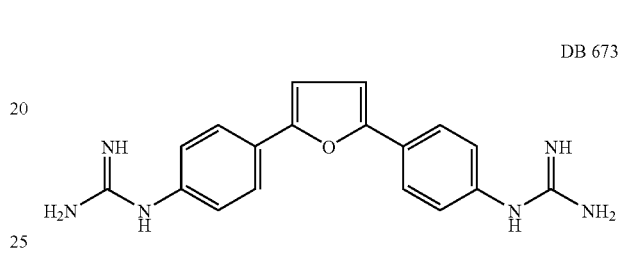
DB 458
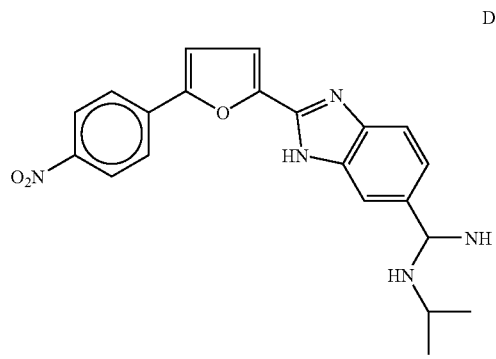
DB680
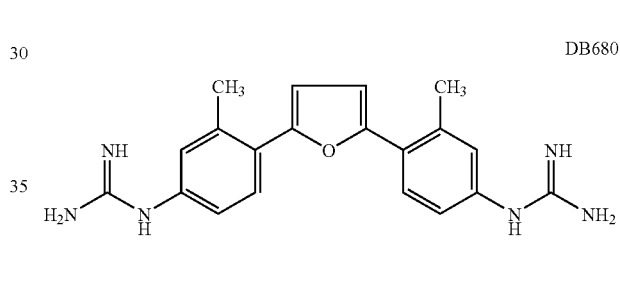
DB 459
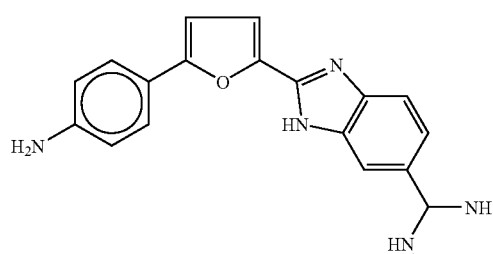
DB 686
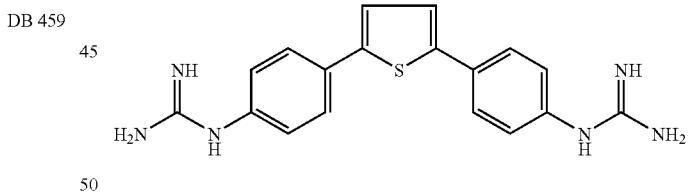
DB 606
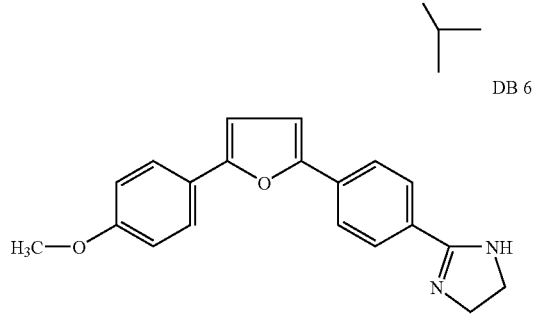
DB 687
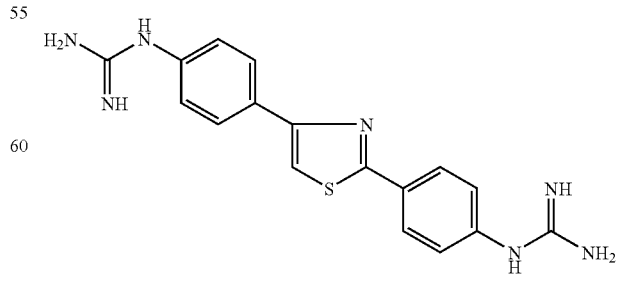

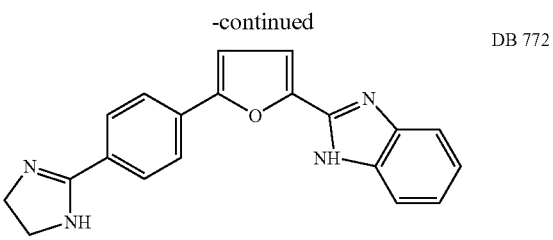

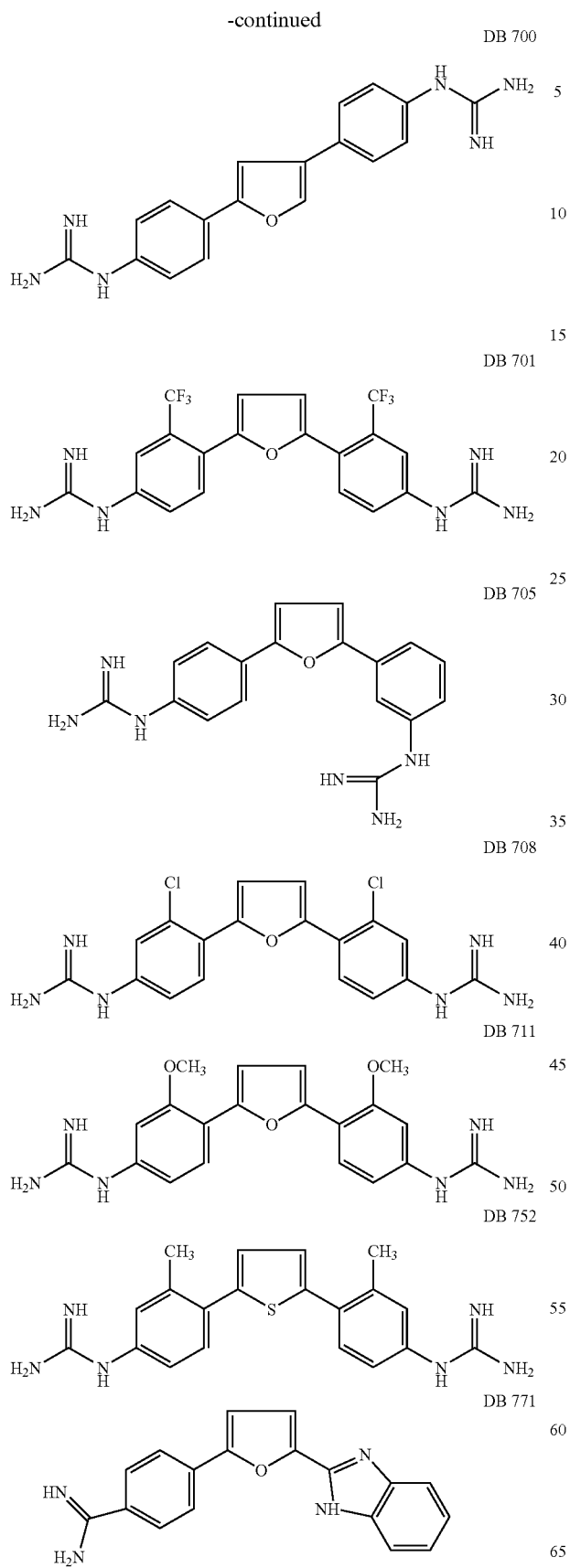

As noted above, the compounds, methods and compositions of the present invention are useful for treating bovine viral diarrhea virus (BVDV) infections and hepatitis C virus (HCV) infections. The term bovine viral diarrhea virus infection means any infection (e.g., acute, latent or persistent) caused by a virus classified as a bovine viral disease virus (BVDV). As set forth above, BVDV is an enveloped, single-stranded, positive sense RNA virus in the genus Pestivirus and the family Flaviviridae. The term bovine viral disease virus (BVDV), as used herein, encompasses all BVDV strains and all serotypes and variants thereof, including live, attenuated, killed or otherwise inactivated forms. The term BVDV specifically includes cytopathic and noncytopathic strains, and strains of both biotype I and biotype II. The term "hepatitis C virus (HCV) infection" includes any infections caused by the hepatitis C virus (HCV), which includes all strains, serotypes and variants of HCV.

In one embodiment of the invention, a subject is administered a therapeutically-effective amount of the compound of formulas (I) through (VI), or a pharmaceutically acceptable salt thereof. A "therapeutically-effective" amount as used herein is an amount of a compound of formulas (I) through (VI) that is sufficient to alleviate (e.g., mitigate, decrease, reduce) at least one of the symptoms associated with BVDV or HCV infection. It is not necessary that the administration of the compound eliminate the symptoms of BVDV or HCV, as long as the benefits of administration of compound outweigh the detriments. Likewise, the terms "treat" and "treating" in reference to BVDV or HCV, as used herein, are not intended to mean that the avian subject is necessarily cured of BVDV or HCV or that all clinical signs thereof are eliminated, only that some alleviation or improvement in the condition of the subject is effected by administration of the compound of Formulas (I) through (VI).

Suitable subjects of the present invention include humans and animals. When the subject is an animal, mammals are preferred, with livestock (e.g., cattle, pigs, sheep, horses) and primates (e.g., monkeys, apes) being particularly preferred. In embodiments of the present invention where BVD are treated, bovine subjects (e.g., cows, bulls, calves) are preferred. In embodiments of the present invention where HCV infections are treated, humans are the preferred subjects. Subjects may be adult, adolescent, juvenile, infant, or neonatal. In one embodiment of the invention, the subject is a live embryo, and may be in utero or in vitro (in the case of an embryo being maintained for in vitro fertilizations.

Subjects may be administered the compounds and compositions of the present invention by any suitable means. Exemplary means are oral administration (e.g., in the form of a liquid or solid), intramuscular injection, subcutaneous injection, and intravenous injection. Pharmaceutical formulations of the present invention comprise active compounds of the invention in a pharmaceutically acceptable carrier. Suitable pharmaceutical formulations include those suitable for inhalation, oral, rectal, topical, (including buccal, sublingual, dermal, vaginal and intraocular), parenteral (including subcutaneous, intradermal, intramuscular, intravenous and intraarticular) and transdermal administration. The most suitable route of administration in any given case may depend upon the anatomic location of the condition being treated in the subject, the nature and severity of the condition being treated, and the particular active compound which is being used. The formulations may conveniently be presented in unit dosage form and may be prepared by any of the methods well known in the art.

In methods of the present invention where treatment is carried out during an in vitro fertilization (IVF) procedure, the compounds may be administered to the embryo by adding the active compound, in a suitable concentration, to the medium in which the embryo is being obtained.

In the manufacture of a medicament according to the invention (the "formulation"), active compounds or the pharmaceutically acceptable salts thereof (the "active compounds") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 99% by weight of the active compound. One or more active compounds may be incorporated in the formulations of the invention, which formulations may be prepared by any of the well known techniques of pharmacy consisting essentially of admixing the components, optionally including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I)-Formula (VI), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound of salt. When the compound or salt is substantially water-insoluble, a sufficient amount of emulsifying agent which is physiologically acceptable may be employed in sufficient quantity to emulsify the compound or salt in an aqueous carrier.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the pharmaceutically active compounds identified with the methods described herein may be lyophilized to produce a lyophilizate which may be reconstituted with a pharmaceutically acceptable carrier, such as water, to regenerate a liposomal suspension.

In addition to the active compounds, the pharmaceutical formulations may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical formulations of the present invention may be lyophilized using techniques well known in the art.

Pharmaceutical formulations of the present invention may comprise compounds of the present invention in lyophilized form. Alternatively, pharmaceutical formulations of the present invention may comprise compounds of the present invention in a pharmaceutically acceptable carrier. Such pharmaceutical formulations are generally made by admixing the compounds described herein with a pharmaceutically acceptable carrier. Pharmaceutically acceptable carriers are preferably liquid, particularly aqueous, carriers, the selection of which are known in the art. For the purpose of preparing such formulations, the compound may be mixed in a buffered saline (e.g., pH 6 to 8) or conventional culture media. The formulation may be stored in a sterile glass container sealed with a rubber stopper through which liquids may be injected and formulation withdrawn by syringe.

With respect to all the methods described herein, a therapeutically effective dosage of any specific compound, the use of which is in the scope of present invention, may vary somewhat from compound to compound and subject to subject, and will depend upon the condition of the subject and the route of delivery. A dosage from about 1 mg/kg to about 15 mg/kg of subject body weight, or about 20 mg/kg of subject body weight, or even about 25 mg/kg of subject body weight may be employed for intravenous injection or oral administration.

The concentration of the compound of the present invention or a pharmaceutically acceptable salt thereof in a formulation of the present invention may be determined by the skilled artisan and will vary according to certain conditions, including the characteristics of subject being treated (e.g., species, age, weight), the severity and type of the infecting virus or the strain that the subject is being vaccinated against, the dosage form being used, and the like.

The compounds of the present invention may be administered in conjunction with other antiviral compounds, as may be determined by the skilled artisan.

The present invention is explained in greater detail in the Examples which follow. These examples are intended as illustrative of the invention, and are not to be taken as limiting thereof.

EXAMPLES 1-12

Synthesis of Inventive Compounds

In the following Examples, compound numbers (compounds 2, 5, 5a, etc.) refer to compounds with structures that are set forth in FIG. 1.

EXAMPLE 1

General Methodology: Chemical Synthesis and Analysis

Melting points were determined with a MEL-TEMP® 3.0 capillary melting point apparatus and are uncorrected. $^1$H nuclear magnetic resonance spectra were recorded on a Varian Unity+300 or a Varian VRX 400 instrument, with peak assignments relative to residual DMSO (2.49 ppm) or CHCl$_3$ (7.24 ppm). Mass spectra were recorded on a VG Instruments 70-SE spectrometer at the Georgia Institute of Technology, Atlanta, Ga. Elemental analyses were performed by Atlantic Microlab, Norcross, Ga. All final compounds were dried in vacuo (oil pump) at 50-60° C. for at least 36 hours before elemental analysis. Unless otherwise stated, all reagent chemicals and solvents (including anhydrous solvents) were purchased from Aldrich Chemical Co., Fisher Scientific, or Lancaster Synthesis and used as received. Acetonitrile (CaH$_2$), triethylamine (CaH$_2$), and ethanol (Mg/I$_2$) were distilled from the indicated drying agent. 2,6-Dimethyl-4-nitrobromobenzene and S-(2-Naphthylmethyl) thioacetimidate were prepared according to the literature. See B. M. Wepster, *Rec. Trav. Chim.* 73, 809-818 (1954); D. N. Kravtsov, *J. Organometal. Chem.* 36, 227-237 (1972); B. G. Shearer et al., *Tetrahedron Lett.* 38, 179-182 (1997).

EXAMPLE 2

Preparation of 2,5-bis(4-nitrophenyl)furans

The following representative procedures are variations of a general procedure previously described in A. Kumar et al., *Heterocyclic Comm.* 5, 301-304 (1999).

2,5-Bis(2-methyl-4-nitrophenyl)furan (Compound 2b). To a solution of 2-bromo-5-nitrotoluene (4.32 g, 20 mmol) and tetrakis(triphenylphospine) palladium (0) (0.40 g) in anhydrous 1,4-dioxane (50 ml) was added 2,5-bis(tri-n-butylstannyl)furan (6.46 g, 10 mmol) and the mixture was heated overnight under nitrogen at 95-100° C. The resulting orange suspension was diluted with hexanes (15 ml), cooled to room-temperature, and filtered to give, after rinsing with hexanes, an orange solid (3.10 g), mp 241-243° C. The product was recrystallized from DMF (100 ml) to give a bright orange fluffy solid (2.87 g, 85%), mp 242-243° C. $^1$H NMR (DMSO-d$_6$): 2.69 (s, 6H), 7.31 (s, 2H), 8.12 (m, 4H), 8.23 (s, 2H). Anal. Calcd. for C$_{18}$H$_{14}$N$_2$O$_5$ (338.31): C, H, N.

2,5-Bis(4-nitrophenyl)furan (Compound 2a). Yield: 88%; orange fluffy solid; mp 269-270° C. (not recrystallized), lit. mp 270-272° C., Ling, C. et al., *J. Am. Chem. Soc.* 1994, 116, 8784-8792.

2,5-Bis(2-methoxy-4-nitrophenyl)furan (Compound 2c). Yield: 77%; bright orange granular solid; mp 308-310° C. (DMF). $^1$H NMR (DMSO-d$_6$): 4.10 (s, 6H), 7.37 (s, 2H), 7.90 (s, 2H), 7.94 (d, 2H), 8.22 (d, 2H). Anal. Calcd. for C$_{18}$H$_{14}$N$_2$O$_7$.0.1H$_2$O (372.11): C, H, N.

2,5-Bis(2-chloro-4-nitrophenyl)furan (Compound 2d). Yield: 71%; fluffy orange solid; mp 247-247.5° C. (DMF/MeOH). $^1$H NMR (DMSO-d$_6$): 7.70 (s, 2H), 8.29 (dd, J=8.8, 2.2 Hz, 2H), 8.36 (d, J=8.8 Hz, 2H), 8.43 (d, J=2.2 Hz, 2H). Anal. Calcd. for C$_{16}$H$_8$Cl$_2$N$_2$O$_5$ (379.15): C, H, N.

2,5-Bis(4-nitro-2-trifluoromethylphenyl)furan (Compound 2e). Yield: 74%; fluffy golden needles; mp 158.5-159° C. (EtOH). $^1$H NMR (DMSO-d$_6$): 7.38 (s, 2H), 8.24 (d, J=8.7 Hz, 2H), 8.57 (d, J=2.4 Hz, 2H), 8.62 (dd, J=8.6, 2.4 Hz, 2H). Anal. Calcd. for C$_{18}$H$_8$F$_6$N$_2$O$_5$ (446.26): C, H, N.

2,5-Bis(2,6-dimethyl-4-nitrophenyl)furan (Compound 2f). Yield: 65%; yellow needles; mp 156.5-157.5° C. (DMF/EtOH/H$_2$O). $^1$H NMR (DMSO-d$_6$): 2.34 (s, 12H), 6.85 (s, 2H), 8.04 (s, 4H). Anal. Calcd. for C$_{20}$H$_{18}$N$_2$O$_5$ (366.36): C, H, N.

EXAMPLE 3

Preparation of 2,5-bis(4-aminophenyl)furans

The following procedures are representative.

2,5-Bis(4-amino-2-methylphenyl)furan (Compound 3b). To a suspension of the bis-nitro derivative 2b (2.87 g) in EtOAc (90 ml) and dry EtOH (10 ml) was added Pd/C (10%) (0.40 g) and the mixture was hydrogenated on a Parr apparatus at an initial pressure of ~50 psi. After the uptake of hydrogen subsided (generally 3-6 hours), the resulting solution was filtered over Celite and the pale yellow to colorless filtrate was concentrated in vacuo to near dryness to give, after dilution with hexanes, the pure diamine as a pale yellow/green solid (2.17 g, 91%), mp 174-176° C., which required no purification. $^1$H NMR (DMSO-d$_6$): 2.33 (s, 6H), 5.15 (br s, 4H), 6.42 (s, 2H), 6.46 (m, 4H), 7.35 (d, 2H). MS (EI): m/z 278 (M$^+$).

2,5-Bis(4-aminophenyl)furan (Compound 3a). Yield: 94%; pale green/tan solid; mp 218-221° C., lit[46] mp 213-216° C. MS (EI): m/z 250 (M+).

2,5-Bis(4-amino-2-methoxyphenyl)furan (Compound 3c). The original oil was reconcentrated with benzene to give a yellow/tan solid which was triturated with ether. Yield: 79%; mp 201-202.5° C. $^1$H NMR (DMSO-$d_6$): 3.80 (s, 6H), 5.25 (br s, 4H), 6.24 (dd, J=8.3, 2.0 Hz, 2H), 6.30 (d, J=1.9 Hz 2H), 6.56 (s, 2H), 7.48 (d, J=8.4 Hz, 2H). MS (EI): m/z 310 (M+).

2,5-Bis(4-amino-2-trifluoromethylphenyl)furan (Compound 3e). Original red oil crystallized from EtOAc/hexanes in two crops as a red/orange solid. Combined yield: 81%; mp (first/major crop) 89.5-91° C.; mp (second crop) 91.5-92° C. $^1$H NMR (DMSO-$d_6$): 5.79 (br s, 4H), 6.52 (s, 2H), 6.82 (dd, J=8.4, 2.4 Hz, 2H), 6.98 (d, J=2.2 Hz, 2H), 7.43 (d, J=8.4 Hz, 2H). MS (EI): m/z 386 (M+).

2,5-Bis(4-amino-2,6-dimethylphenyl)furan (Compound 3f). Yield: 99%; white fluffy solid; mp 144.5-146° C. $^1$H NMR (DMSO-$d_6$): 2.01 (s, 6H), 5.06 (br s, 4H), 6.24 (s, 2H), 6.29 (s, 4H). MS (EI): m/z 306 (M+).

2,5-Bis(4-amino-2-chlorophenyl)furan (Compound 3d). To a suspension of the corresponding bis-nitro derivative 2d (1.22 g, 3.2 mmol) in dry EtOH (100 ml) and DMSO (20 ml) was added $SnCl_2.2H_2O$ (5.80 g, 25.7 mmol) and the mixture was heated under nitrogen at 80° C. After 4-5 hours, TLC showed that starting material had been consumed, and thus the mixture was cooled, neutralized with NaOH (aq), and extracted with EtOAc. The extract was washed with water, brine, then dried ($Na_2SO_4$) and concentrated. The resulting oil was crystallized from benzene/hexane with partial concentration to give a light brown solid (0.74 g, 71%), mp 191.5-193° C. Catalytic hydrogenation was not explored. $^1$H NMR (DMSO-$d_6$): 5.60 (br s, 4H), 6.61 (dd, J=8.6, 2.2 Hz, 2H), 6.68 (d, J=2.2 Hz 2H), 6.82 (s, 2H), 7.56 (d, J=8.6 Hz, 2H). MS (EI): m/z 318 (M+).

EXAMPLE 4

Preparation of 2,5-bis(4-N,N'-di-BOC-guanidinophenyl)furan derivatives

The following procedures are representative.

2,5-Bis(4-N,N'-di-BOC guanidinophenyl)furan (Compound 4a). To a room-temperature solution of 2,5-bis(4-aminophenyl)furan (0.626 g, 2.5 mmol) and 1,3-bis(tert-butoxycarbonyl)-2-methyl-2-thiopseudourea (1.56 g, 5.3 mmol) in anhydrous DMF was added triethylamine (1.59 g, 15.7 mmol) followed by mercury(II) chloride (1.57 g, 5.8 mmol) and the resulting suspension was stirred at room-temperature for 22 hours. After diluting with $CH_2Cl_2$ and sodium carbonate solution, the suspension was filtered over Celite and the filtrate was washed well with water (3×) and finally with brine. After drying ($Na_2SO_4$), the solvent was removed in vacuo and the residue was diluted with MeOH to give the BOC-protected bis-guanidine as a pale yellow solid. The collected product was purified by reprecipitation from $CH_2Cl_2$/MeOH to give a fluffy yellow solid (1.25 g, 68%), mp >400° C. dec. $^1$H NMR ($CDCl_3$): 1.50 and 1.53 (2s, 36H), 6.65 (s, 2H), 7.66 (s, 8H), 10.38 (br s, 2H), 11.61 (br s, 2H).

2,5-Bis(2-methyl-4-N,N'-di-BOCguanidinophenyl)furan (Compound 4b). Yellow solid, mp >250° C. dec. Yield: 62%. $^1$H NMR ($CDCl_3$): 1.51 and 1.52 (2s, 36H), 2.53 (s, 6H), 6.60 (s, 2H), 7.40 (s, 2H), 7.62 (d, 2H), 7.74 (d, 2H), 10.34 (s, 2H), 11.62 (br s, 2H).

2,5-Bis(2-methoxy-4-N,N'-di-BOCguanidinophenyl)furan (Compound 4c). Yellow solid, mp >300° C. dec. Yield: 79%. $^1$H NMR ($CDCl_3$): 1.50 and 1.53 (2s, 36H), 3.95 (s, 6H), 6.95 (s, 2H), 7.13 (d, 2H), 7.59 (s, 2H), 7.86 (d, 2H), 10.36 (s, 2H), 11.55 (br s, 2H).

2,5-Bis(2-chloro-4-N,N'-di-BOCguanidinophenyl)furan (Compound 4d). Pale yellow/tan solid, mp >400° C. dec. Yield: 63%. $^1$H NMR ($CDCl_3$): 1.52 (s, 36H), 7.17 (s, 2H), 7.63 (dd, 2H), 7.79 (d, 2H), 7.88 (d, 2H), 10.43 (s, 2H), 11.59 (br s, 2H).

2,5-Bis(2-trifluoromethyl-4-N,N'-di-BOC guanidinophenyl)furan (Compound 4e). Bright orange solid. Yield: 88%. $^1$H NMR ($CDCl_3$): 1.51 and 1.53 (2s, 36H), 6.77 (s, 2H), 7.82 (d, 2H), 7.94 (s, 2H), 8.00 (d, 2H), 10.52 (s, 2H), 11.59 (br s, 2H).

2,5-Bis(2,6-dimethyl-4-N,N'-di-BOC guanidinophenyl)furan (Compound 4f). Pale yellow/off-white solid, mp >300° C. dec. Yield: 89%. $^1$H NMR ($CDCl_3$): 1.51 and 1.53 (2s, 36H), 2.23 (s, 12H), 6.31 (s, 2H), 7.33 (s, 4H), 10.27 (s, 2H), 11.63 (br s, 2H).

EXAMPLE 5

Deprotection of N,N'-di-BOC guanidines

The following procedures are representative, and are further illustrated in FIG. 1.

2,5-Bis(4-guanidinophenyl)furan-dihydrochloride (Compound 5a). A solution of the corresponding N,N'-di-BOCguanidine (1.19 g, 1.62 mmol) in $CH_2Cl_2$ (15 ml) was diluted with dry EtOH (10 ml) and saturated at ice-water bath temperature with anhydrous HCl. The solution was then stirred at room-temperature for 2-3 days (drying tube), with the product slowly precipitating (shorter reaction times generally gave incomplete deprotection). The resulting suspension was concentrated to near dryness, with the solid then taken up in hot EtOH. After filtering to clarify, the solution was concentrated to near dryness to give a suspension, which was diluted with ether and collected to yield, after drying in vacuo at 50-60° C. for 2 days, the bis-guanidine dihydrochloride as an off-white/tan solid (0.66 g, quantitative), mp >300° C. dec. $^1$H NMR (DMSO-$d_6$): 7.12 (s, 2H), 7.31 (d, 4H), 7.58 (br s, 8H), 7.86 (d, 4H), 10.09 (br s, 2H). MS (FAB, thioglycerol): m/z 335.3 (MH+, 100). Anal. Calcd. for $C_{18}H_{18}N_6O.2HCl.0.25EtOH$ (407.30): C, H, N.

2,5-Bis(4-guanidino-2-methylphenyl)furan dihydrochloride (Compound 5b). Tan solid, mp 265-271° C. dec. $^1$H NMR (DMSO-$d_6$): 2.53 (s, 6H), 6.93 (s, 2H), 7.17 (m, 4H), 7.56 (br s, 8H), 7.82 (d, 2H), 10.06 (br s, 2H). MS (FAB, thioglycerol): m/z 363.3 (MH+, 100). Anal. Calcd. for $C_{20}H_{22}N_6O.2HCl.1.5H_2O.0.66EtOH$ (496.93): C, H, N.

2,5-Bis(4-guanidino-2-methoxyphenyl)furan dihydrochloride (Compound 5c). Light brown solid. $^1$H NMR (DMSO-$d_6$): 3.95 (s, 6H), 6.92 (dd, 2H), 6.99 (d, 2H), 7.02 (s, 2H), 7.58 (br s, 8H), 7.95 (d, 2H), 10.08 (br s, 2H). MS (EI): m/z 352 (M+—$NH_2CN$, 38.0), 310 (100), 267 (38.9), 251 (8.8), 155 (18.7). Anal. Calcd. for $C_{20}H_{22}N_6O_3.2HCl.1.0H_2O.0.33EtOH$ (500.57): C, H, N.

2,5-Bis(2-chloro-4-guanidinophenyl)furan dihydrochloride (Compound 5d). Tan solid, mp 300-304° C. dec. $^1$H NMR (DMSO-$d_6$): 7.31 (s, 2H), 7.33 (d, 2H), 7.47 (s, 2H), 7.72 (br s, 8H), 8.04 (d, 2H). MS (DCI, ammonia): m/z 365, 363, 361 (MH+—$NH_2CN$, 8, 52, 78), 323, 321, 319 (11, 66, 100). Anal. Calcd. for $C_{18}H_{16}Cl_2N_6O.2HCl.0.5H_2O$ (485.21): C, H, N, Cl.

2,5-Bis(4-guanidine-2-trifluoromethylphenyl)furan dihydrochloride (Compound 5e). Orange/red solid. $^1$H NMR (DMSO-d$_6$): 6.99 (s, 2H), 7.63 (d, 2H), 7.69 (s, 2H), 7.79 (br s, 8H), 7.91 (d, 2H), 10.37 (br s, 2H). MS (CI, isobutane): m/z 471 (MH$^+$, 14), 429 (100), 387 (19). Anal. Calcd. for C$_{20}$H$_{16}$F$_6$N$_6$O.2HCl.0.67H$_2$O.0.67EtOH (586.24): C, H, N.

2,5-Bis(4-guanidino-2,6-dimethylphenyl)furan dihydrochloride (Compound 5f). Off-white solid. $^1$H NMR (DMSO-d$_6$): 2.20 (s, 12H), 6.56 (s, 2H), 7.01 (s, 4H), 7.57 (br s, 8H), 10.09 (br s, 2H). MS (FAB, thioglycerol): m/z 391.2 (MH$^+$, 100). Anal. Calcd. for C$_{22}$H$_{26}$N$_6$O.2HCl.0.5H$_2$O (472.41): C, H, N.

EXAMPLE 6

Preparation of 2-[5(6)-Amidino-2-benzimidazoyl]-5-(4-nitrophenyl)furan

A mixture of 5-(4-nitrophenyl)furfural (0.651 g, 0.003 mol), 4-amidino-1,2-phenylenediamine (0.614 g, 0.003 mol) and 1,4-benzoquinone (0.324 g, 0.003 mol) in 40 ml of ethanol (under nitrogen) was heated at reflux for 8 h. The volume of the reaction mixture was reduced to 20 ml under reduced pressure, cooled and the resultant solid was collected by filtration. The solid was washed with cold ethanol and ether. The product was dried to yield the mono hydrochloride salt 0.8 g (70%). The mono salt (0.65 g) was dissolved in 120 ml of ethanol and acidified with HCl-saturated ethanol and after standing overnight in a refrigerator the resultant solid was filtered, washed with ether and dried for 24 h in a vacuum oven at 70° C. to yield 0.6 g (85%) mp 300° C. $^1$H NMR (DMSO-d$_6$): 9.3 (br s, 2H), 9.09 (br s, 2H), 8.33 (d, J=7.6 Hz, 2H), 8.20 (d, J=7.6 Hz 2H), 8.19 (s,1H), 7.79 (d, J=8.4 Hz, 1H), 7.73 (d, J=8.4 Hz, 1H), 7.56 (d, J=3.6 Hz, 1H), 7.51 (d, J=3.6 Hz 1H). $^{13}$C NMR (DMSO-d$_6$): 165.9, 152.6, 146.4, 145.4, 145.3, 141.6, 138.7, 134.7, 124.6, 124.0, 122.1, 121.5, 116.0, 114.6, 114.0, 111.9. FABMS m/e 348(M$^+$ +1). Anal. Calcd for C$_{18}$H$_{13}$N$_5$O$_3$.2HCl.: C, 51.44; H, 3.59; N, 16.66. Found: C, 51.24; H, 4.03; N, 16.92.

EXAMPLE 7

Preparation of 2-[5(6)-amidino-2-benzimidazoyl]-5-(4-aminophenyl)furan

The above nitro analog (0.5 g, 0.0013 mol) and 0.3 g of 10% Pd/C in 130 ml of methanol was subjected to hydrogenation at 50 psi for 4 h. The catalyst was removed by filtration over filteraid and the solvent was removed under reduced pressure. The solid was taken up in methanolic HCl, warmed on a water bath for 0.5 h and the solvent was removed under reduced pressure. The residue was treated with ether and the solid was collected by filtration and dried under vacuum at 75° C. for 12 h to yield 0.44 g (73%) mp >360° C. $^1$H NMR (DMSO-d$_6$/D$_2$O): 8.07 (d, J=1.6 Hz, 1H), 7.74(d, J=8.4 Hz, 2H), 7.66 (dd, J=1.6 and 8.4 Hz 2H), 7.39 (d, J=3.6 Hz, 1H), 6.91 (d, J=3.6 Hz, 1H),6.89 (d, J=8.4 Hz, 2H). $^{13}$C NMR (DMSO-d$_6$/D$_2$O): 166.2, 156.7, 145.8, 142.0, 141.0, 138.1, 126.2, 123.2, 122.3, 119.2, 116.6, 116.0, 115.1, 107.5. FABMS m/e 318(M$^+$ +1). Anal. Calcd. for C$_{18}$H$_{15}$N$_5$O.3HCl.2H$_2$O: C, 43.59; H, 6.09; N, 16.92. Found: C, 43.71; H, 6.01; N, 16.81.

EXAMPLE 8

Preparation of 2-[5 (6)-{2-imidazolinyl}-2-benzimidazoyl]-5-(4-nitrophenyl)furan A mixture of 5-(4-nitrophenyl)furfural (0.434 g, 0.002 mol), 4-(2-imidazolinyl)-1,2-phenylenediamine hydrochloride hydrate (0.461 g, 0.002 mol) and 1,4-benzoquinone (0.216 g, 0.002 mol) in 40 ml of ethanol (under nitrogen) was heated at reflux for 8 h. The volume of the reaction mixture was reduced to 20 ml under reduced pressure, cooled and the resultant solid was collected by filtration. The solid was washed with cold ethanol and ether. The product was dried to yield 0.52 g (63%). The compound was dissolved in 200 ml of ethanol and acidified with HCl-saturated ethanol and was stirred at room temperature for 3 h. The mixture was cooled on ice and the solid was filtered, washed with ether and dried for 24 h in a vacuum oven at 75° C. to yield 0.51 g (90%) mp >300° C. $^1$H NMR (DMSO-d$_6$/D$_2$0): 8.31 (d, J=8.4 Hz, 2H), 8.30 (s, 1H), 8.15 (d, J=8.4 Hz, 2H), 7.81 (s, 2H), 7.52 (d, J=4.0 Hz, 1H), 7.46 (d, J=4.0 Hz, 1H), 4.03 (s,4H). $^{13}$C NMR (DMSO-d$_6$/D$_2$0): 165.6, 153.1, 146.8, 145.7, 145.2, 134.7, 124.9, 124.2, 122.8, 116.9, 115.8, 115.1, 115.0, 112.1, 105.6, 104.7, 44.2. FABMS m/e 374 (M$^+$ +1). Anal. Calcd for C$_{20}$H$_{15}$N$_5$O$_3$.2HCl: C, 53.82; H, 3.88; N, 15.69. Found: C, 53.94; H, 3.93; N, 15.84.

EXAMPLE 9

Preparation of 2-[5 (6)-{2-imidazolinyl}-2-benzimidazoyl]-5-(4-aminophenyl)furan The mono hydrochloride salt of the above nitro analog (0.5 g, 0.0013 mol) and 0.2 g of 10% Pd/C in 130 ml of methanol was subjected to hydrogenation at 50 psi for 4 h. The catalyst was removed by filtration over filteraid, washed with warm methanol. The solvent volume was reduced to approximately half under reduced pressure. The flask containing the solution was placed in an ice bath and saturated with HCl gas. The mixture was stirred at room temperature for 4 h and treated with dry ether and the solid was collected by filtration. The solid was dried under vacuum at 75° C. for 24 h to yield 0.55 g (86%) mp >300° C. $^1$H NMR (DMSO-d$_6$/D$_2$0): 8.24 (d, J=1.2 Hz 1H), 7.88 (d, J=8.0 Hz, 2H), 7.80 (s, 2H), 7.51(d, J=3.6 Hz, 1H), 7.21 (d, J=8.4 Hz, 2H), 7.10 (dd, J=1.2, 3.6 Hz, 1H), 4.0 (s,4H). $^{13}$C NMR (DMSO-d$_6$/D$_2$0): 165.8, 156.4, 145.8, 142.0, 140.9, 137.9, 126.2, 123.7, 121.0, 117.0, 116.8, 115.3, 108.5, 44.6. FABMS m/e 344(M$^+$ +1). Anal. Calcd for C$_{20}$H$_{17}$N$_5$O.3HCl$_2$.1H$_2$O: C, 48.96; H, 4.97; N, 14.27. Found: C, 48.58; H, 4.32; N, 14.27.

EXAMPLE 10

Preparation of 2-[5 (6)-{N-isopropylamidino}-2-benzimidazoyl]-5-(4-nitrophenyl)furan A mixture of 5-(4-nitrophenyl)furfural (0.434 g, 0.002 mol), 4-N-isopropylamidino-1,2-phenylenediamine hydrochloride hydrate (0.493 g, 0.002 mol) and 1,4-benzoquinone (0.216 g, 0.002 mol) in 40 ml of ethanol (under nitrogen) was heated at reflux for 6 h. The volume of the reaction mixture was reduced to about 15 ml under reduced pressure, the mixture was cooled and the resultant solid was collected by filtration to yield the mono hydrochloride salt 0.66 g (80%). The mono salt was dissolved in 100 ml of ethanol and acidified with HCl-saturated ethanol and after cooling in an ice bath the resultant solid was filtered, washed with ether and dried for 24 h in a vacuum oven at 75° C. to yield 0.7 g (91%) mp >300° C. $^1$H NMR (DMSO-d$_6$/D$_2$0): 8.26 (d, J=8.8 Hz, 2H), 8.11 (d, J=8.8 Hz 2H), 8.01 (d, J=1.2 Hz, 1H), 7.77 (d, J=8.8 Hz; 1H), 7.59 (dd, J=1.2, 8.8 Hz; 1H), 7.50(d, J=7.6 Hz, 1H), 7.42 (d, J=7.6 Hz 1H), 4.04 (septet, J=6.8 Hz,1H), 1.3(d, J=6.8 Hz,6H). $^{13}$C NMR (DMSO-d$_6$): 162.7, 153.8, 147.2, 145.2, 144.8, 140.7, 138.2, 135.2, 125.4, 124.7, 124.0, 123.5, 116.3, 115.9, 115.3, 112.6, 45.6, 21.4. FABMS m/e 376(M$^+$+1). Anal. Calcd for $C_{21}H_{19}N_5O_3 \cdot 2HCl \cdot 2.0H_2O$: C, 49.71; H, 5.16; N, 13.80. Found: C, 49.65; H, 5.11; N, 13.50.

EXAMPLE 11

2-[5(6)-N-isopropylamidino-2-benzimidazoyl]-5-(4-aminophenyl)furan

The mono hydrochloride salt of the above nitro analog (0.411 g, 0.001 mol) and 0.3 g of 10% Pd/C in 120 ml of methanol was subjected to hydrogenation at 50 psi for 4 h. The catalyst was removed by filtration over filteraid, washed with warm methanol. The solvent volume was reduced to approximately half under reduced pressure. The flask containing the solution was placed in an ice bath and saturated with HCl gas. The mixture was stirred at room temperature for 4 h and treated with dry ether and the solid was collected by filtration. The solid was dried under vacuum at 80° C. for 24 h to yield 0.41 g (87%) mp >300° C. $^1$H NMR (DMSO-d$_6$/D$_2$O): 8.04 (d, J=1.6 Hz, 1H), 7.91 (d, J=8.4 Hz 2H), 7.80 (d, J=8.4 Hz 1H), 7.64 (dd, J=1.6, 8.4 Hz, 1H), 7.60 (d, J=4.0 Hz, 1H), 7.24(d, J=8.4 Hz, 2H), 7.14 (d, J=4.0 Hz 1H), 4.05 (septet, J=6.4 Hz,1H), 1.3(d, J=6.4 Hz,6H). $^{13}$C NMR (DMSO-d$_6$): 162.4, 156.8, 144.4, 140.9, 138.8, 137.6, 135.0, 126.3, 125.4, 124.6, 124.1, 121.1, 118.0, 115.6, 114.9, 108.6, 45.6, 21.3. FABMS m/e 360(M$^+$ +1). Anal. Calcd for $C_{21}H_{21}N_5O_3 \cdot 3HCl$: C, 53.80; H, 5.15; N, 14.93. Found: C, 54.22; H, 4.75; N, 15.05.

EXAMPLE 12

2,5-Bis(2-Benzimidazolyl-4-cyanophenyl)furan

A mixture of 5-[4-cyanophenyl]-2-furancarboxaldehyde (1.97, 0.01 mol), 1,2-phenylenediamine (1.06 g, 0.01 mol) and 1,4-benzoquinone (1.08 g, 0.01 mol) in 50 ml dry ethanol was heated at reflux (under nitrogen) for 8 h. The reaction mixture was cooled and diluted with ether and filtered. The solid was collected and stirred with 1:3 mixture of EtOH and ether for 20 min and the yellow brown solid was filtered, washed with ether and dried in vacuum at 70° C. for 12 h. which yielded 1.96 g (69%), mp 227-8° C. dec, $^1$H-NMR (DMSO-d6): 8.06 (d, 2H, J=8.8 Hz), 7.91(d, 2H,J=8.8 Hz), 7.60 (dd, 2H, J=3.2 Hz, J=6.4 Hz), 7.38 (d, 1H, J=3.6 Hz), 7.32(d, 1H, J=3.6 Hz), 7.23 (dd, 2H, J=3.2 Hz, J=6.4 Hz). $^{13}$C-NMR(DMSO-d6): 152.1, 146.0, 142.7, 138.7, 133.2, 132.6, 124.1, 122.3, 118.4, 114.9, 112.5, 111.1, 109.8, MS: m/e 285 (M+). Anal. calcd. for: C18H11N3O: C, 75.79; H, 3.86; N, 14.73. Found: C, 75.88; H, 3.77; N, 14.55.

2,5-Bis[2-Benzimidazolyl-4-(amidino)phenyl]furan dihydrochloride

The above cyano compound (2.85 g, 0.01 mol) in 60 ml ethanol was saturated with dry HCl gas at 0-5° C. The reaction mixture was stirred at room temperature for 12 days (monitored by IR and TLC). The mixture was diluted with ether and the yellow imidate ester hydrochloride was filtered, washed with ether and dried under vacuum for 6 h 3.73 g (92%). The solid was used in next step without further purification. A suspension of the imidate ester hydrochloride (0.808 g, 0.002 mol) in 35 ml ethanol was saturated with ammonia gas at 0-5° C. and stirred for 24 h at room temperature. The solvent was reduced to one-third under reduced pressure, diluted with ether and filtered. The yellow solid was resuspended in 10 ml ethanol and treated with 4 ml saturated ethanolic HCl and stirred at 3.5° C. for 2 h. The solvent was removed under vacuum and the residue triturated with ether, filtered, washed with ether and dried under vacuum at 45° C. for 24 h to yield 0.61 g (81%) yellow solid mp >280° C. dec. $^1$H-NMR (DMSO-d6/D2): 8.15(d, 2H, J=8.7 Hz), 7.93 (d, 2H, J=8.7 Hz), 7.78 (d, 1H, J=3.6 Hz), 7.75 (dd, 2H, J=3 Hz, J=6.3 Hz), 7.50 (d, 1H, J=3.6 Hz), 7.49 (dd, 1H, J=3 Hz, J=6.3 Hz). $^{13}$C-NMR(DMSO-d6): 165.0, 155.9, 139.8, 139.7, 133.4, 132.4, 129.3, 127.8, 126.3, 125.2, 119.5, 114.3, 112.0. FABMS: m/e 303 (M++1). Anal. calcd. for: C18H14N4O.2HCl: C, 57.61; H, 4.29; N, 14.93. Found; C, 57.45; H, 4.46; N, 14.64.

2,5-Bis[2-Benzimidazolyl4-(2-imidazolino)phenyl] furan dihydrochloride

A mixture of the imidate ester hydrochloride (0.808 g, 0.002 mol) from above, ethylenediamine (0.12 g, 0.002 mol) in 20 ml of dry ethanol was heated at reflux for 12 h. The solvent volume was reduced to 8 ml under reduced pressure and diluted with ether. The resultant solid was filtered and dried. This solid was dissolved in 35 mL hot ethanol and saturated with HCl gas at room temperature. The mixture was stirred at 50° C. for 2 h and concentrated under reduced pressure and 30 ml dry ether was added. The precipitated yellow salt was filtered, washed with ether and dried under vacuum at 70° C. for 24 h to yield 0.69 g (84%) yellow solid mp >300° C. dec. $^1$H-NMR(DMSO-d6/D2): 8.06(d, 2H, J=8.7 Hz), 7.91 (d, 2H, J=8.7 Hz), 7.71 (dd; 2H, J=3 Hz, J=6 Hz), 7.64 (d, 1H, J=3.9 Hz), 7.47(dd, 1H, J=3 Hz, J=6.3 Hz), 7.44 (d, 1H, J=3.9 Hz), 3.94 (s, 4H). $^{13}$C-NMR(DMSO-d6): 164.6, 155.7, 140.3, 140.1, 133.9, 132.9, 129.7, 126.7, 125.4, 122.1, 119.2, 114.6, 112.5, 44.8, FABMS: m/e 303 (M++1). Anal. calcd for: C20H16N4O.2HCl.0.5H2O: C, 58.54; H, 4.67; N, 13.65. Found; C, 58.54; H, 4.67; N, 13.66.

EXAMPLES 13-24

Anti-BVDV Properties of Inventive Compounds

EXAMPLE 13

Screening of Antiviral Compounds for Anti-BVDV Activity 2.0 cm$^2$ wells in a 24-well plate were seeded with 50 μl of medium from 12 ml of MEM-eq (minimum essential medium (MEM) with Earle's salts supplemented with 10% (v/v) equine serum, sodium bicarbonate (0.75 mg/ml), L-glutamine (0.29 mg/ml), penicillin G (100 U/ml), streptomycin (100 μg/ml), and amphotericin B (0.25 μg/ml)), which was derived by trypsinization of a confluent monolayer of Madin Darby Bovine Kidney (MDBK) cells in a 25 cm$^2$ flask. Cells were incubated at 38.5° C. with 5% CO$_2$ for 24 hours. The average number of cells per well was determined and later used to calculate appropriate multiplicities of infection (MOI) of BVDV virus.

Cells were inoculated with BVDV in medium containing test antiviral compounds (12.5 μM, 200 μL total volume), as follows:
- two wells had no BVDV, and no antiviral compound
- one well had BVDV at 0.05 MOI, and no antiviral compound
- one well had BVDV at 1.0 MOI, and no antiviral compound
- ten wells had BVDV at 0.05 MOI, and 12.5 μM of antiviral compound ten wells had BVDV at 1.0 MOI, and 12.5 µM of antiviral compound.

The inoculated cells incubated for one hour at 38.5° C. with 5% $CO_2$ in humidified air. The medium was removed from the wells, and the cells washed one time with $Ca^{2+}$ and $Mg^{2+}$-free PBS comprising antiviral compound (12.5 µM) (cells in the wells not initially treated with antiviral compounds were washed without antiviral compound). One ml of MEM-eq comprising antiviral compound (12.5 µM) was added to wells initially treated with antiviral compound; those not treated with antiviral compound initially did not receive antiviral compound at this step. Three days post-inoculation, medium was removed and stored at −20° C. for assay. One ml of fresh medium containing 200 µL total (12.5 µM) antiviral compound was is added to wells initially treated with antiviral compound; those not treated with antiviral compound initially did not receive antiviral compound at this step. Seven days post-inoculation, medium was removed and stored at −80° C. for serial dilution & assay.

The MDBK cells were resuspended in MEM-eq with no antiviral compound. Uterine tubal cells (UTC) were freeze-thawed and stored at −80° C. for analysis. UTC lysates were serially diluted with medium from Day 7 and assayed by immunoperoxidase for the presence of BVDV.

EXAMPLE 14

Immunoperoxidase Monolayer Assay for BVDV

All samples were assayed for BVDV using the immunoperoxidase monolayer assay as described in A. Afshar et al., Can J Vet Res; 55:91-93 (1991). Samples were assayed in triplicate by adding 50 µL of MEM-eq containing approximately $2.5 \times 10^3$ MDBK cells to 50-µL of each sample supplemented with 50 μL of fresh MEM-eq in a 96-well culture plate. Plates were incubated for 72 h at 38.5° C. in a humidified atmosphere of 5% CO2 and air before the immunoperoxidase labeling technique was performed as follows:

After fixation, potentially infected cells were incubated with monoclonal antibodies D89 (M. L. Vickers et al., *J Vet Diagn Invest* 2, 300-302 (1990); Xue W et al., *J Clin Microbiol* 28, 1688-1693 (19905) specific for E2/gp53, a major envelope glycoprotein of BVDV (Xue W et al., *Vet Microbiol* 57, 105-118 (1997)) and 20.10.6 specific for NS3-p80, a conserved nonstructural protein (W. V. Corapi et al., *Am J Vet Res* 51, 1388-1394 (1990)). After washing with PBS and Tween 20 to remove unbound antibodies, peroxidase-conjugated rabbit anti-mouse IgG (Jackson Immuno Research Lab, West Grove, Pa.) was added. After a short incubation period, unbound peroxidase-conjugated antibody was removed by washing with PBS and Tween 20. Finally, the enzyme substrate, aminoethyl carbazole (Zymed Laboratories, Inc., South San Francisco, Calif.), which produces a reddish-brown color when oxidized by horseradish peroxidase, was added. Color change was visualized under light microscopy and compared to known positive and negative controls on each plate.

EXAMPLE 15

Tissue Culture Passage

All samples other than stock virus aliquots were also passaged in tissue culture to optimize isolation of BVDV. Upon initial thawing, 200 μL of each sample was inoculated onto a 2 $cm^2$ well seeded 24 h previously with MDBK cells. Passages were incubated 5 days (d) at 38.5° C. in an atmosphere of 5% $CO_2$ and humidified air. Passages were frozen at −80° C. for storage. Tissue culture passage samples were thawed and assayed by virus isolation if isolation of BVDV was unsuccessful from the original sample. Samples were reported to be free of BVDV by virus isolation only if virus was not detected after each of two serial passages.

EXAMPLE 16

Reverse Transcription Nested Polymerase Chain Reaction Assay (RT-nPCR)

A reverse transcription nested polymerase chain reaction assay for detecting BVDV was performed on all samples other than stock virus aliquots. Upon initial thawing, RNA was isolated from samples using the QIAamp® viral RNA mini kit (Qiagen, Valencia, Calif.) according to the manufacturer's instructions. RNA samples were stored at −80° C. until RT-nPCR was performed.

All steps of complementary DNA production (cDNA) and amplification were carried out in a single closed-tube reaction using a modification of the protocol of McGoldrick et al. (see Duffell S J et al., Vet Rec 1985; 117:240-245; Givens M D, et al., Theriogenology 2000; 54:1093-1107; Lang-Ree J R, et al., Vet Rec 1994; 135:412-413). In the first step, 5 μL of trehalose (22% w/v stock; Sigma, St Louis, Mo., cat #T5251) was used to store and maintain the following mixture in the lid of a 200-μL, thin-walled tube: 0.4 μL of each inner primer BVD 180 and HCV 368 (50 μM), 1 μL of dNTPs (10 mM) and 0.25 μL of Taq Polymerase (1.25 U, Promega, Madison, Wis.). The tubes were left to dry for 2 h at room temperature prior to storage.

In the second step, the initial reverse transcription polymerase chain reaction was performed in the bottom of the tubes containing the dried trehalose mixture within the lid. Two μL of RNA were added through the overlaid mineral oil (50 μL) to the initial reaction volume (48 μL) containing the following reagents (Promega): 5 μL 10× buffer, 8 μL of MgCl2 (25 mM), 2 μL of dNTPs (10 mM), 1 μL of each outer primer BVD 100 and HCV 368 (5 μM), 1 μL of Triton X-100 (10% stock), 0.25 μL of dithiothreitol (100 mM), 0.25 μL (10 U) RNAsin, 0.5 μL (2.5 U) of Taq polymerase, and 0.5 μL (100 U) of MMLV (Moloney Murine Leukemia Virus), reverse transcriptase. The tubes were then subjected to the following cycle parameters: 37° C. for 45 min. 95° C. for 5 min and then 20 cycles at 94° C. for 1 min, 55° C. for 1 min and 72° C. for 1 min.

A final elongation step of 72° C. for 10 min completed the initial amplification reaction. In the third step, the tubes were inverted several times to mix the samples in the lid and in the base to initiate the nested polymerase chain reaction (nPCR). The tubes were then centrifuged at 14,000×g for 12 sec before returning to the thermocycler for nPCR, using 30 cycles of 94° C. for 1 min, 55° C. for 1 min and 72° C. for 45 sec. A final elongation step of 72° C. for 10 min completed the amplification process prior to maintaining the reactions at 4° C. Five microliter aliquots of PCR products were separated by 1.5% agarose gel electrophoresis. The agarose gels contained 0.5 μg/ml ethidium bromide to allow visualization of RT-nPCR products using an ultraviolet transilluminator.

The outer primers, BVD 100 (5'-GGCTAGCCATGCCCT-TAG-3') (SEQ ID NO. 1) and HCV 368 (5'-CCATGTGC-CATGTACAG-3') (SEQ ID NO. 2) amplified a 290 base pair sequence of the 5' untranslated region of the viral genome. The inner primers, BVD 180 (5'-CCTGAGTA-CAGGGDAGT CGTCA-3') (SEQ ID NO. 3) and HCV 368 amplified a 213 base pair sequence within the first ampilcon. The novel BVD 180 primer was degenerate at the 14th base (D=G+A+T) to accommodate differences within the 5' untranslated sequences of virus strains used in this research as determined by automated dye terminator nucleotide sequencing (Nucleic Acid Resource Facility, Auburn University, Ala.) of the initial PCR products from viral stocks.

EXAMPLE 17

Oocyte Collection and Maturation

Cow ovaries were collected at an abattoir in Omaha, Nebr., and placed in PBS for transport to a nearby laboratory. The contents of 1- to 10-mm follicles were aspirated at a vacuum rate of 21.5 ml/min and poured onto a 70 μm filter. Cellular components of the pooled follicular aspirate were rinsed with TL-HEPES and searched for oocytes surrounded by multiple layers of dense cumulus cells. Useable cumulus oocyte complexes (COCs) were washed two additional times in TL-HEPES, then placed in 7.5 ml of maturation media that had previously equilibrated at 38.5° C. in an atmosphere of 5% $CO_2$ and humidified air. The maturation media was then sealed and maintained at 38.5° C. for 20 to 22 h while being transported to the experimental laboratory.

EXAMPLE 18

Media for In Vitro Fertilization/embryo Assays

Oocytes were matured in cell culture medium 199 (CCM 199) with Earle's salts (GIBCO-BRL, Grand Island, N.Y., USA) supplemented with 10% (v/v) heat-inactivated fetal bovine serum (FBS; HyClone Lab., Inc., Logan, Utah, USA), sodium pyruvate (11 μg/ml), bovine FSH (0.01 U/ml), bovine LH (0.01 U/ml), penicillin (100 U/ml) and streptomycin (100 μg/ml).

Matured oocytes were fertilized in CR2 medium (C. F. Rosenkrans et al., *Theriogenology* 35, 266 (1991)) supplemented with BSA (6 mg/ml), heparin (10 μg/ml), penicillamine (0.3 μg/ml), hypotaurine (0.2 μg/ml), penicillin (100 U/ml) and streptomycin (100 μg/ml).

The first three days (d) of in vitro culture (IVC) was in CR2 medium supplemented with BSA (6 mg/ml), penicillin (100 U/ml) and streptomycin (100 μg/ml). The last four d of IVC was in CR2 medium supplemented with 10% (v/v) FBS, penicillin (100 U/ml) and streptomycin (100 μg/ml).

EXAMPLE 19

Exposure to Bovine Viral Diarrhea Virus (BVDV)

After in vitro maturation (IVM), COCs were washed 5 times in 3 ml of MEM-eq. After washing, COCs were exposed to a noncytopathic strain of BVDV in 3 ml of MEM-eq or maintained separately as negative controls in BVDV-free MEM-eq. Exposed and unexposed COCs were incubated for 1 h at 38.5° C. in an atmosphere of 5% CO2 and humidified air, and then washed 3 times in 3 ml of TL-HEPES before addition to IVF drops.

The noncytopathic strains of BVDV used in this research included 2 diverse Genotype I strains (SD-1 and NY-1) and 2 diverse Genotype II strains (CD-87 and PA-131). Givens M D et al., *Theriogenology* 2000; 54:1093-1107. All stocks were propagated in BVDV-free MDBK cells cultured in MEM-eq. Virus was harvested by freezing and thawing and was stored in cryovials at –80° C. until needed.

EXAMPLE 20

In Vitro Fertilization

Matured COCs were placed in 42-μL drops of fertilization medium under mineral oil. Cryopreserved bovine semen from a single collection was used for fertilization. This semen was confined to be free of BVDV by virus isolation and RT-nPCR. After PERCOLL®-gradient (45 to 90%) separation, $1.5 \times 10^5$ spermatozoa were added to each fertilization drop, which was incubated for approximately 18 h at 38.5° C. in a humidified atmosphere of 5% $CO_2$ and air.

EXAMPLE 21

In Vitro Culture

After the IVF period, presumptive zygotes were removed, washed 4 times in TL-Hepes, equilibrated in IVC medium with BSA, and placed with cumulus cells still attached in 30-μl drops (10 to 12 per drop) of the IVC medium with BSA under mineral oil. The IVC plates were incubated for 3 d at 38.5° C. in a humidified atmosphere of 5% $CO_2$ and air. After the first 3 d in IVC, embryos were washed 3 times in TL-Hepes, and most of the cumulus cells were removed by gentle aspiration in and out of a sterile pipette. The nearly nude embryos were examined for cleavage, and those at the 5-cell stage or greater were washed 1 more time in IVC medium and placed with pieces of detached cumulus in 60-μl drops (20 to 25 per drop) of the IVC medium with 10% (v/v) FBS under mineral oil. These developed embryos were incubated an additional 4 d. After the final 4 d in IVC, embryos were transferred into 3 ml of MEM-eq, separated from cumulus cells, and development to the morula or blastocyst stage was noted.

EXAMPLE 22

Washing and Trypsin Treatment of Embryos

Washing and trypsin treatment of Day 7 embryos conformed to procedures recommended by the International Embryo Transfer Society for treatment of in vivo-derived bovine embryos. (Stringfellow D A, et al., *Manual of the International Embryo Transfer Society Third Edition*, Savoy I L: International Embryo Transfer Society, 1998; 79-84). Degenerate and developed Day 7 embryos were washed 12 times in 1 ml of MEM-eq in 2-cm2 wells.

For trypsin treatment, twelve 3-ml washes in 35-mm Petri dishes were used. The first 5 and last 5 washes were PBS supplemented with 0.4% BSA, penicillin (100 U/ml) and streptomycin (100 μg/ml). The 6th and 7th washes were trypsin diluted 1:250 in 3 ml of Hank's balanced salt solution without $Ca^{2+}$ and $Mg^{2+}$. Embryos were treated in trypsin for approximately 90 sec (45 sec/wash) before proceeding through the last 5 washes.

EXAMPLE 23

Samples Assayed for BVDV

During each of 12 research replicates (3 replicates with 4 diverse strains of BVDV), 140 to 180 COCs were exposed to virus while 50 to 80 COCs were maintained as negative controls. For each replicate, samples were obtained from exposed and unexposed cultures to be assayed for BVDV. All samples other than stock virus aliquots were assayed for BVDV using virus isolation with (a) immunoperoxidase assay for viral detection, (b) tissue culture passage prior to virus isolation to optimize viral detection, and (c) RT-nPCR. Samples included:

Stock virus aliquots. The viral aliquot to which the COCs were exposed was serially diluted and assayed by virus isolation using immunoperoxidase assay.

Day 3 cumulus cells. On Day 3 of IVC, some detached cumulus cells were removed from the 3rd wash of TL-Hepes, transferred into 3 ml of MEM-eq, and then placed in 500 μL of MEM-eq within a cryovial. Cells were lysed by freezing at −80° C. and thawing to release any intracellular virus prior to assay for BVDV.

Day 7 cumulus cells. On Day 7 of IVC, cumulus cells from exposed and unexposed cultures were transferred from the 3 ml of MEM-eq into 500 μL of MEM-eq within a cryovial. Cells were lysed by freezing at −80° C. and thawing to release any intracellular virus prior to assay for BVDV.

Day 7 individual embryos. If sufficient numbers of BVDV-exposed M/B developed by Day 7 of each research replicate, a group of 10 M/B was washed as previously described and a group of 10 M/B was trysin-treated as previously described. Virus-exposed, washed M/B were individually placed into 500 μL of MEM-eq (4 to 5 per replicate) or were individually cryopreserved and thawed before placement in MEM-eq (4 to 5 per replicate). Virus-exposed, trypsin-treated M/B were individually placed into 500 μL of MBM-eq (3 to 5 per replicate) or were individually cryopreserved and thawed before placement in MEM-eq (4 to 5 per replicate). All samples were sonicated before viral assay.

If sufficient numbers of non-exposed M/B developed by Day 7 of each replicate, a group of 10 M/B was washed as previously described. Non-exposed, washed M/B were individually placed directly into 500 μL of MBM-eq (5 per replicate) or were individually cryopreserved and thawed before placement in MEM-eq (5 per replicate). Samples were sonicated before viral assay.

EXAMPLE 24

Statistical Analysis and Results

The tissue culture infective dose 50% ($TCID_{50}$)/ml of the exposure aliquot was determined by the method of Reed and Muench (L. J. Reed and H. Muench, *Am J Hygiene* 27, 493-497 (1938). Results of viral detection assays were compared using a Pearson Chi-square test statistic (J. Sall and A. Lehman, *JMP Start Statistics* (Duxbury Press, Belmont, Calif. (1996), 195-211).

Table 2 sets forth the results of the analysis of in vitro culture media and cell lysates that have been treated with the indicated antiviral compound for the indicated time at a concentration of 12.5 μM, after exposure to BVDV at a MOI of 0.05 (see Example 12).

TABLE 2

| Antiviral drug | Day 3 Media | | Day 7 Media | | Day 7 Cell Lysates | |
|---|---|---|---|---|---|---|
| | $TCID_{50}$/mL | % Control | $TCID_{50}$/mL | % Control | $TCID_{50}$/mL | % Control |
| No antiviral | 2.00E+05 | | 5.20E+05 | | 2.00E+06 | |
| DB619 | 3.50E+02 | 0.18% | 2.00E+05 | 38.46% | 1.10E+06 | 55.00% |
| DB673 | 1.00E+02 | 0.05% | 6.20E+03 | 1.19% | 3.50E+04 | 1.75% |

Table 3 sets forth the results of the analysis of in vitro culture media and cell lysates that have been treated with the indicated antiviral compound for the indicated time at a concentration of 12.5 μM, after exposure to BVDV at a MOI of 1.0 (see Example 12).

TABLE 3

| Antiviral drug | Day 3 Media | | Day 7 Media | | Day 7 Cell Lysates | |
|---|---|---|---|---|---|---|
| | $TCID_{50}$/mL | % Control | $TCID_{50}$/mL | % Control | $TCID_{50}$/mL | % Control |
| No antiviral | 3.50E+05 | | 3.50E+04 | | 6.20E+05 | |
| DB619 | 6.20E+04 | 17.71% | 3.50E+04 | 100.00% | 3.50E+05 | 56.45% |
| DB673 | 3.50E+02 | 0.10% | 2.00E+05 | 571.43% | 2.70E+05 | 43.55% |

Table 4, below sets forth the results of the analysis of Day 3 in vitro culture media and Day 3 cell lysate that has been treated with the indicated antiviral compound at a concentration of 12.5 μM, after exposure to BVDV at a MOI of 0.5 (see Example 12).

TABLE 4

| Antiviral drug | Day 3 Media | | Day 3 Cell Lysates | |
|---|---|---|---|---|
| | $TCID_{50}$/mL | % Control | $TCID_{50}$/mL | % Control |
| No antiviral | 3.50E+06 | | 6.20E+06 | |
| DB 457 | 1.00E+02 | 0.0029% | 3.50E+02 | 0.0056% |
| DB 458 | Negative | | Negative | |

TABLE 4-continued

| Antiviral drug | Day 3 Media | | Day 3 Cell Lysates | |
|---|---|---|---|---|
| | TCID$_{50}$/mL | % Control | TCID$_{50}$/mL | % Control |
| DB 459 | Negative | | 1.00E+02 | 0.0016% |
| DB 606 | Negative | | Negative | |
| DB 680 | Negative | | Negative | |
| DB 701 | 6.20E+03 | 0.1771% | 3.50E+04 | 0.5645% |
| DB 705 | Negative | | Negative | |
| DB 708 | Negative | | Negative | |
| DB 711 | 2.40E+05 | 6.8571% | 2.00E+07 | 322.5806% |
| DB 752 | Negative | | 6.20E+02 | 0.01% |

Table 5 sets forth the results of the analysis of Day 3 cell lysates that have been treated with the indicated antiviral compound for three days at the indicated concentration, after exposure to BVDV at a MOI of 0.05.

TABLE 5

| Antiviral drug | Day 3 Media | | Day 3 Cell Lysates | |
|---|---|---|---|---|
| | TCID$_{50}$/mL | % Control | TCID$_{50}$/mL | % Control |
| No antiviral | 2.00E+06 | | 3.50E+05 | |
| DB 456 25 μm | 3.50E+03 | 0.1750% | 2.00E+03 | 0.5714% |
| DB 456 12 μm | 6.20E+02 | 0.0310% | 3.50E+03 | 1.0000% |
| DB 456 6 μm | 3.50E+04 | 1.7500% | 3.50E+04 | 10.0000% |
| DB 456 3 μm | 3.50E+05 | 17.5000% | 6.20E+05 | 177.1429% |
| DB 456 1.5 μm | 5.10E+05 | 25.5000% | 3.50E+06 | 1000.0000% |
| DB 456 0.7 μm | 6.30E+05 | 31.5000% | 3.50E+06 | 1000.0000% |
| DB 456 0.4 μm | 6.30E+05 | 31.5000% | 3.50E+06 | 1000.0000% |
| DB 456 0.2 μm | 6.30E+05 | 31.5000% | 3.50E+05 | 100.0000% |

In the specification, and examples there have been disclosed typical preferred embodiments of the invention and, although specific terms are employed, they are used in a generic and descriptive sense only and not for the purposes of limitation, the scope of the invention being set forth in the following claims.

That which is claimed is:

1. A compound according to Formula I:

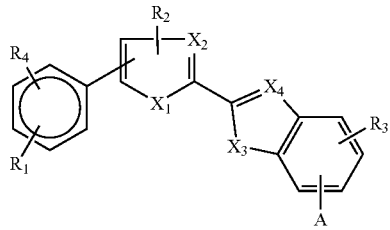

wherein:
$X_1$ and $X_3$ are each independently selected from the group consisting of O, S and $NR_9$, wherein $R_9$ is H or alkyl;
$X_2$ and $X_4$ are each independently CH or N, wherein when $X_1$ is O, $X_3$ is $NR_9$ and $X_4$ is N, $X_2$ is N;
A is selected from the group consisting of

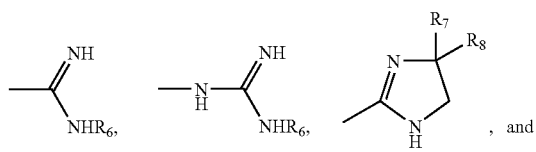

$R_1$, $R_2$, $R_3$, and $R_4$ are each independently selected from the group consisting of H, alkyl, alkoxy, halide, alkylhalide, nitro and amino groups;
$R_6$ is H, alkyl or aryl; and
$R_7$ and $R_8$ are each independently selected from the group consisting of H and alkyl.

2. The compound according to claim 1, wherein A is

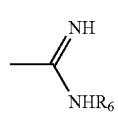

and $R_6$ is alkyl.

3. The compound according to claim 1, wherein A is

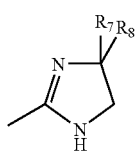

and $R_7$ and $R_8$ are each H.

4. The compound according to claim 1, wherein $R_1$ is an amino group.

5. The compound according to claim 1, wherein $R_1$ is a nitro group.

6. A pharmaceutical composition comprising a compound of claim 1, in a pharmaceutically acceptable carrier.

7. The pharmaceutical composition according to claim 6, wherein the composition is formulated for intravenous administration.

8. The pharmaceutical composition according to claim 6, wherein the composition is formulated for oral administration.

9. A compound according to Formula II:

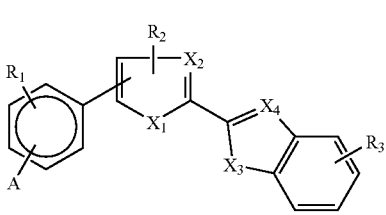

wherein:
$X_1$ and $X_3$ are each independently selected from the group consisting of O, S and $NR_9$, wherein $R_9$ is H or alkyl;
$X_2$ and $X_4$ are each independently CH or N, wherein when $X_1$ is O, $X_3$ is $NR_9$ and $X_4$ is N, $X_2$ is N;
A is selected from the group consisting of

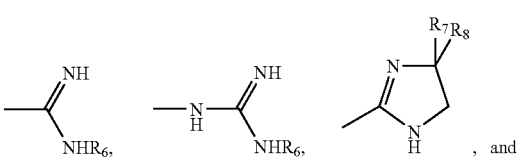

$R_1$, $R_2$, and $R_3$ are each independently selected from the group consisting of H, alkyl, alkoxy, halide, alkylhalide, nitro and amino groups;
$R_6$ is H, alkyl or aryl; and
$R_7$ and $R_8$ are each independently selected from the group consisting of H and alkyl.

10. A pharmaceutical composition comprising a compound of claim 9, in a pharmaceutically acceptable carrier.

11. The pharmaceutical composition according to claim 10, wherein the composition is formulated for intravenous administration.

12. The pharmaceutical composition according to claim 10, wherein the composition is formulated for oral administration.

13. A method of treating bovine viral diarrhea virus (BVDV) infection in a subject in need of such treatment, comprising administering to the subject a compound selected from the group consisting of Formula I and Formula II:

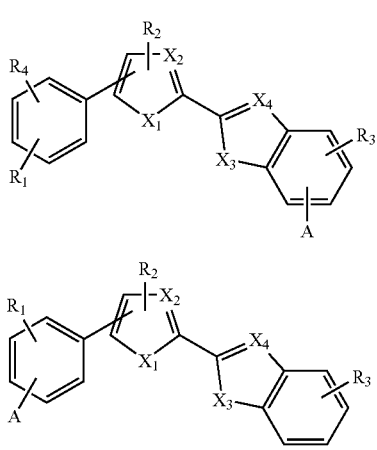

(I)

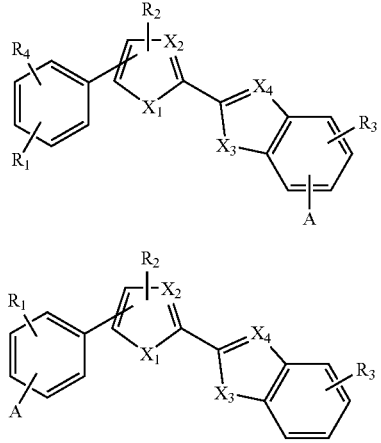

(I)

(II)

(II)

wherein:

X$_1$ and X$_3$ are each independently selected from the group consisting of O, S and NR$_9$, wherein R$_9$ is H or alkyl;

X$_2$ and X$_4$ are each independently CH or N, wherein when X$_1$ is O, X$_3$ is NR$_9$ and X$_4$ is N, X$_2$ is N;

A is selected from the group consisting of

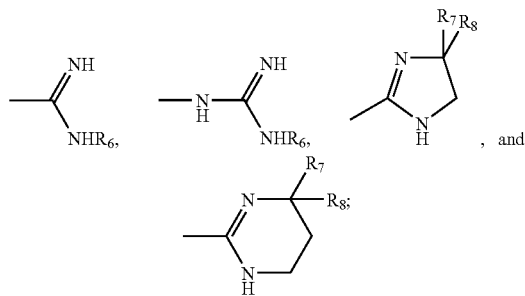

, and

X$_1$ and X$_3$ are each independently selected from the group consisting of O, S and NR$_9$, wherein R$_9$ is H or alkyl;

X$_2$ and X$_4$ are each independently CH or N, wherein when X$_1$ is O, X$_3$ is NR$_9$ and X$_4$ is N, X$_2$ is N;

A is selected from the group consisting of

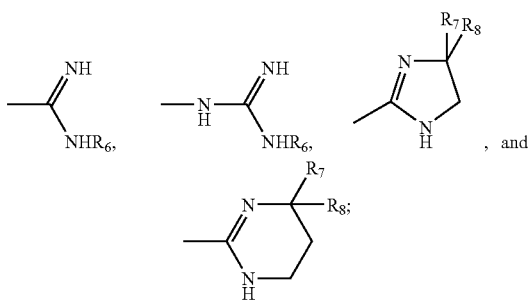

, and

R$_1$, R$_2$, R$_3$, and R$_4$ are each independently selected from the group consisting of H, alkyl, alkoxy, halide, alkylhalide, amidine, nitro and amino groups;

R$_6$ is H, alkyl or aryl; and

R$_7$ and R$_8$ are each independently selected from the group consisting of H and alkyl;

or a pharmaceutically acceptable salt thereof, in an amount sufficient to treat the bovine viral diarrhea virus (BVDV) infection.

14. The method according to claim 13, wherein the compound is a compound of Formula I.

15. The method according to claim 13, wherein the subject is a cow.

16. The method according to claim 13, wherein the subject is an embryo.

17. The method according to claim 13, wherein the compound is administered intravenously.

18. The method according to claim 13, wherein the compound is administered orally.

19. A method of treating hepatitis C infection in a subject in need of such treatment, comprising administering to the subject a compound selected from the group consisting of Formula I and Formula II:

R$_1$, R$_2$, R$_3$, and R$_4$ are each independently selected from the group consisting of H, alkyl, alkoxy, halide, alkylhalide, amidine, nitro and amino groups;

R$_6$ is H, alkyl or aryl; and

R$_7$ and R$_8$ are each independently selected from the group consisting of H and alkyl;

or a pharmaceutically acceptable salt thereof, in an amount sufficient to treat the hepatitis C infection.

20. The method according to claim 19, wherein the compound is a compound of Formula I.

21. The method according to claim 19, wherein the subject is a human.

22. The method according to claim 19, wherein the compound is administered intravenously.

23. The method according to claim 19, wherein the compound is administered orally.

24. A method of treating an infection of a member of the Flaviviridae family of viruses in a subject in need of such treatment, wherein the member of the Flaviviridae family of viruses is a virus of the genus Pestivirus or is Hepatitis C virus (HCV). the method comprising administering to the subject a compound selected from the group consisting of Formula I and Formula II:

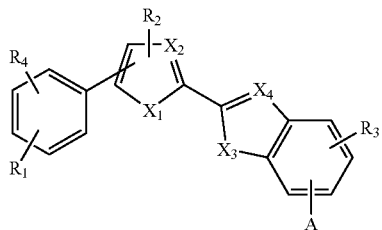

(I)

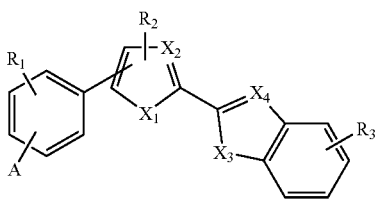

(II)

wherein
  $X_1$ and $X_3$ are each independently selected from the group consisting of O, S and $NR_9$, wherein $R_9$ is H or alkyl;
  $X_2$ and $X_4$ are each independently CH or N;
  A is selected from the group consisting of

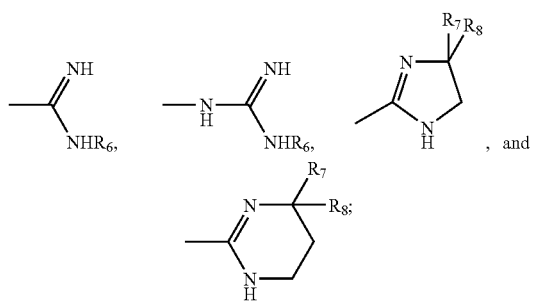

$R_1, R_2, R_3,$ and $R_4$ are each independently selected from the group consisting of H, alkyl, alkoxy, halide, alkylhalide, amidine, nitro and amino groups;
  $R_6$ is H, alkyl or aryl; and
  $R_7$ and $R_8$ are each independently selected from the group consisting of H and alkyl;
or a pharmaceutically acceptable salt thereof, in an amount sufficient to treat the infection.

25. The method according to claim 24, wherein the compound is a compound of Formula II.

26. The method according to claim 24, wherein the compound is represented by the formula:

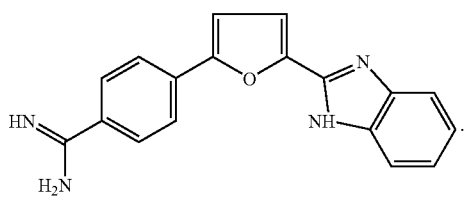

27. The method according to claim 24, wherein the compound is represented by the formula:

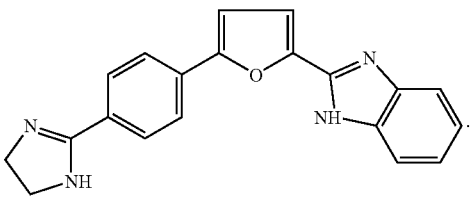

28. The method according to claim 24, wherein the compound is administered intravenously.

29. The method according to claim 24, wherein the compound is administered orally.

30. A method of treating a culture for bovine viral diarrhea virus (BVDV) infection, comprising administering to the culture a compound selected from the group consisting of Formula (I)-Formula (II):

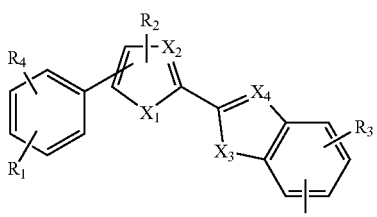

(I)

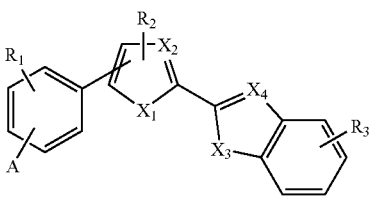

(II)

wherein:
  $X_1$ and $X_3$ are each independently selected from the group consisting of O, S and $NR_9$, wherein $R_9$ is H or alkyl;
  $X_2$ and $X_4$ are each independently CH or N;
  A is selected from the group consisting of

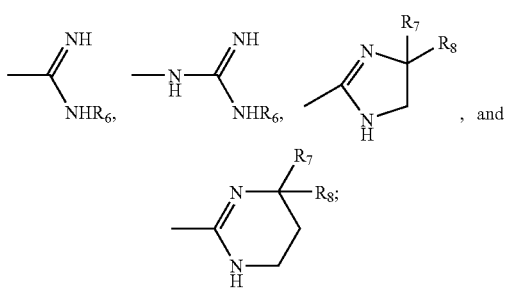

$R_1, R_2, R_3,$ and $R_4$ are each independently selected from the group consisting of H, alkyl, alkoxy, amidine, halide, alkylhalide, nitro and amino groups;

$R_6$ is H, alkyl or aryl; and $R_7$ and $R_8$ are each independently selected from the group consisting of H and alkyl; or a pharmaceutically acceptable salt thereof, in an amount sufficient to treat the BVDV infection.

31. The method of claim 30, wherein the culture is selected from one of a cell culture and a tissue culture.

32. A method of treating an embryo for bovine viral diarrhea virus (BVDV) infection, comprising administering to the embryo a compound selected from the group consisting of Formula (I)-Formula (II):

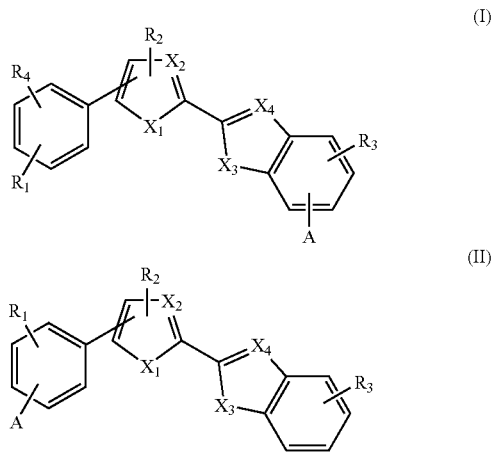

(I)

(II)

wherein:

$X_1$ and $X_3$ are each independently selected from the group consisting of O, S and $NR_9$, wherein $R_9$ is H or alkyl;

$X_2$ and $X_4$ are each independently CH or N;

A is selected from the group consisting of

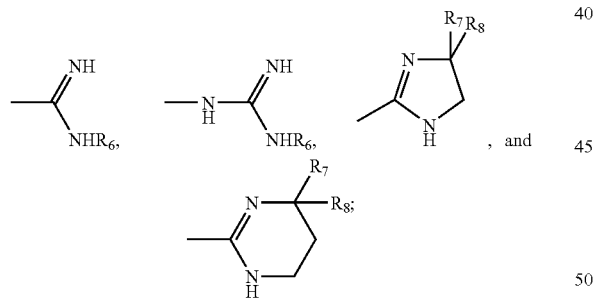

$R_1, R_2, R_3$, and $R_4$ are each independently selected from the group consisting of H, alkyl, alkoxy, amidine, halide, alkylhalide, nitro and amino groups;

$R_6$ is H, alkyl or aryl; and $R_7$ and $R_8$ are each independently selected from the group consisting of H and alkyl; or a pharmaceutically acceptable salt thereof, in an amount sufficient to treat the BVDV infection.

33. The method of claim 32, wherein the embryo comprises an in vitro-produced embryo.

34. A method of treating bovine viral diarrhea virus (BVDV) in a culture medium surrounding an in vitro-produced embryo, comprising administering to the culture medium a compound selected from the group consisting of Formula (I)-Formula (II):

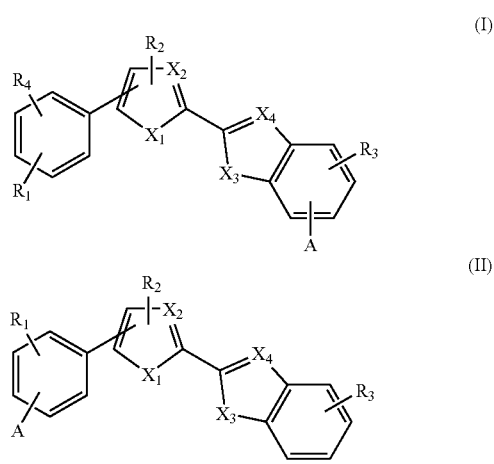

(I)

(II)

wherein:

$X_1$ and $X_3$ are each independently selected from the group consisting of O, S and $NR_9$, wherein $R_9$ is H or alkyl;

$X_2$ and $X_4$ are each independently CH or N;

A is selected from the group consisting of

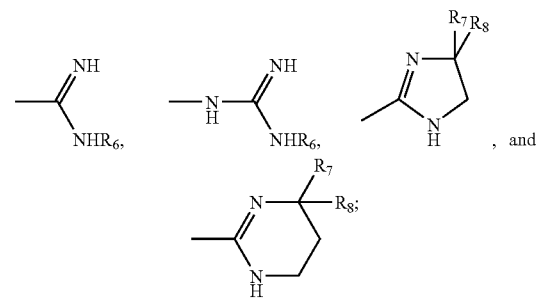

$R_1, R_2, R_3$, and $R_4$ are each independently selected from the group consisting of H, alkyl, alkoxy, amidine, halide, alkylhalide, nitro and amino groups;

$R_6$ is H, alkyl or aryl; and $R_7$ and $R_8$ are each independently selected from the group consisting of H and alkyl; or a pharmaceutically acceptable salt thereof, in an amount sufficient to treat the BVDV.

35. The method according to claim 13, wherein the compound is a compound of Formula II.

36. The method of claim 16, wherein the embryo is an in vitro-produced embryo.

37. The method according to claim 19, wherein the compound is a compound of Formula II.

38. The method according to claim 13, wherein the compound is administered topically.

* * * * *

UNITED STATES PATENT AND TRADEMARK OFFICE
CERTIFICATE OF CORRECTION

PATENT NO. : 7,410,989 B2  Page 1 of 1
APPLICATION NO. : 11/602031
DATED : August 12, 2008
INVENTOR(S) : Dykstra et al.

It is certified that error appears in the above-identified patent and that said Letters Patent is hereby corrected as shown below:

On title page, item 75 Inventors
replace "Arvid Kumar"
with --Arvind Kumar--.

On title page, item 75 Inventors
replace "Chad F. Stephens"
with --Chad E. Stephens--.

On title page, item 75 Inventors
replace "Villa Roca, GA (US)"
with --Villa Rica, GA (US)--.

On column 1, line 26
replace "Al33383"
with --Al33363--.

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,410,989 B2
APPLICATION NO. : 11/602031
DATED : August 12, 2008
INVENTOR(S) : Dykstra et al.

Page 1 of 1

It is certified that error appears in the above-identified patent and that said Letters Patent is hereby corrected as shown below:

On column 1, line 26
replace "grant number K08 AI01728-01 and U0I-A133383 from the"
with --Grant Nos. K08 AI001728-01 and U01-AI033363 awarded by the--.

On column 1, line 27
replace "United States government"
with --government--.

On column 1, line 28
replace "may have"
with --has--.

Signed and Sealed this
Twelfth Day of June, 2012

David J. Kappos
*Director of the United States Patent and Trademark Office*